US010428165B2

(12) United States Patent
Sookraj

(10) Patent No.: US 10,428,165 B2
(45) Date of Patent: Oct. 1, 2019

(54) SYSTEMS AND PROCESSES FOR POLYACRYLIC ACID PRODUCTION

(71) Applicant: Novomer, Inc., Boston, MA (US)

(72) Inventor: Sadesh H. Sookraj, Cambridge, MA (US)

(73) Assignee: Novomer, Inc., Boston, MA (US)

(*) Notice: Subject to any disclaimer, the term of this patent is extended or adjusted under 35 U.S.C. 154(b) by 10 days.

(21) Appl. No.: 15/550,111

(22) PCT Filed: Feb. 12, 2016

(86) PCT No.: PCT/US2016/017844
§ 371 (c)(1),
(2) Date: Aug. 10, 2017

(87) PCT Pub. No.: WO2016/130977
PCT Pub. Date: Aug. 18, 2016

(65) Prior Publication Data
US 2018/0057619 A1    Mar. 1, 2018

Related U.S. Application Data

(60) Provisional application No. 62/116,229, filed on Feb. 13, 2015.

(51) Int. Cl.
C08F 20/06    (2006.01)
C07C 51/12    (2006.01)
(Continued)

(52) U.S. Cl.
CPC .............. C08F 20/06 (2013.01); C07C 51/12 (2013.01); C07C 51/14 (2013.01); C07C 51/145 (2013.01);
(Continued)

(58) Field of Classification Search
CPC .... C08F 20/06; C08F 2/01; C08F 2/18; C07C 51/12; C07C 51/377; C07C 51/14; C07C 51/147; C07C 57/04; C07C 59/01
(Continued)

(56) References Cited

U.S. PATENT DOCUMENTS 3,169,945 A    2/1965    Hostettler et al.
3,678,069 A    7/1972    Busler
(Continued)

FOREIGN PATENT DOCUMENTS

WO    2003/050154 A2    6/2003
WO    2004/089923 A1    10/2004
(Continued)

OTHER PUBLICATIONS

Agostini et al., "Synthesis and Characterization of Poly-β-Hydroxybutyrate. I. Synthesis of Crystalline DL-Poly-β-Hydroxybutyrate from DL-β-Butyrolactone", Journal of Polymer Science, Part A-1, vol. 9, No. 10, 1971, pp. 2775-2787.
(Continued)

Primary Examiner — Michael Bernshteyn
(74) Attorney, Agent, or Firm — Morrison & Foerster LLP

(57) ABSTRACT

Disclosed are systems and methods for the production of polyacrylic acid and superabsorbent polymers from ethylene oxidation to form ethylene oxide. Reacting the ethylene oxide with carbon monoxide to form to beta propiolactone (BPL) or polypropiolactone (PPL), or a combination thereof. An outlet configured to provide a carbonylation stream comprising the BPL or PPL, or a combination thereof and using one or more reactors to convert BPL to acrylic acid or to convert at least some of the BPL to PPL, and then to convert PPL to acrylic acid. An outlet configured to provide a PPL stream to a second reactor tm to convert at least some
(Continued)

of the PPL to AA or a third reactor to convert at least some of the PPL to AA. The outlet configured to provide an AA stream to a fourth reactor to convert the AA to polyacrylic acid.

13 Claims, 1 Drawing Sheet

(51) Int. Cl.
```
C07C 51/14      (2006.01)
C07C 51/377     (2006.01)
C07C 51/145     (2006.01)
C07C 57/04      (2006.01)
C07C 59/01      (2006.01)
C08F 2/01       (2006.01)
C08F 2/18       (2006.01)
```
(52) U.S. Cl.
CPC ............ *C07C 51/377* (2013.01); *C07C 57/04* (2013.01); *C07C 59/01* (2013.01); *C08F 2/01* (2013.01); *C08F 2/18* (2013.01)
(58) Field of Classification Search
USPC ........................................................ 526/317
See application file for complete search history.

(56) References Cited

U.S. PATENT DOCUMENTS

| | | | |
|---|---|---|---|
| 5,310,948 A | 5/1994 | Drent et al. | |
| 5,359,081 A | 10/1994 | Drent et al. | |
| 5,648,452 A | 7/1997 | Schechtman et al. | |
| 6,133,402 A | 10/2000 | Coates et al. | |
| 6,316,590 B1 | 11/2001 | Coates et al. | |
| 6,538,101 B2 | 3/2003 | Coates et al. | |
| 6,608,170 B1 | 8/2003 | Coates | |
| 6,852,865 B2 | 2/2005 | Coates et al. | |
| 7,420,064 B2 | 9/2008 | Luinstra et al. | |
| 8,445,703 B2 | 5/2013 | Allen et al. | |
| 8,796,475 B2 | 8/2014 | Allen et al. | |
| 9,096,510 B2 | 8/2015 | Porcelli et al. | |
| 9,156,803 B2 | 10/2015 | Allen et al. | |
| 9,206,144 B2 | 12/2015 | Allen et al. | |
| 9,327,280 B2 | 5/2016 | Lee et al. | |
| 9,403,788 B2 | 8/2016 | Lee et al. | |
| 9,493,391 B2 | 11/2016 | Allen et al. | |
| 9,914,689 B2 | 3/2018 | Porcelli et al. | |
| 10,099,988 B2 | 10/2018 | Farmer et al. | |
| 10,099,989 B2 | 10/2018 | Sookraj | |
| 2005/0014977 A1 | 1/2005 | Drent et al. | |
| 2007/0161806 A1 | 7/2007 | Preishuber-Pflugl et al. | |
| 2012/0123137 A1 | 5/2012 | Allen et al. | |
| 2013/0165670 A1 | 6/2013 | Allen et al. | |
| 2013/0281715 A1 | 10/2013 | Allen et al. | |
| 2014/0275575 A1 | 9/2014 | Allen et al. | |
| 2014/0296522 A1 | 10/2014 | Lee et al. | |
| 2014/0309399 A1* | 10/2014 | Porcelli .................. | C07C 51/09 528/359 |
| 2015/0005513 A1 | 1/2015 | Lee et al. | |
| 2015/0141693 A1 | 5/2015 | Allen et al. | |
| 2015/0299083 A1 | 10/2015 | Porcelli et al. | |
| 2015/0368394 A1 | 12/2015 | Allen | |
| 2016/0016876 A1 | 1/2016 | Mahoney | |
| 2016/0102040 A1 | 4/2016 | Allen et al. | |
| 2016/0102068 A1 | 4/2016 | Allen et al. | |
| 2016/0288057 A1 | 10/2016 | Lapointe et al. | |
| 2017/0029352 A1 | 2/2017 | Ruhl et al. | |
| 2017/0073463 A1 | 3/2017 | Lee et al. | |
| 2017/0080409 A1 | 3/2017 | Farmer et al. | |
| 2017/0096407 A1 | 4/2017 | Sookraj | |
| 2017/0107103 A1 | 4/2017 | Sookraj et al. | |
| 2017/0145126 A1 | 5/2017 | Mahoney | |
| 2017/0225157 A1 | 8/2017 | Lee | |
| 2017/0247309 A1 | 8/2017 | Porcelli et al. | |
| 2018/0016219 A1 | 1/2018 | Farmer et al. | |
| 2018/0022677 A1 | 1/2018 | Sookraj et al. | |
| 2018/0029005 A1 | 2/2018 | Sookraj et al. | |
| 2018/0030014 A1 | 2/2018 | Sookraj et al. | |
| 2018/0030015 A1 | 2/2018 | Farmer et al. | |
| 2018/0030201 A1 | 2/2018 | Farmer et al. | |
| 2018/0094100 A1 | 4/2018 | Farmer et al. | |
| 2018/0354881 A1 | 12/2018 | Farmer et al. | |
| 2018/0354882 A1 | 12/2018 | Sookraj | |

FOREIGN PATENT DOCUMENTS

| | | | | |
|---|---|---|---|---|
| WO | 2010/118128 A1 | 10/2010 | | |
| WO | 2012/030619 A1 | 3/2012 | | |
| WO | 2012/158573 A1 | 11/2012 | | |
| WO | 2013/063191 A1 | 5/2013 | | |
| WO | 2013/122905 A1 | 8/2013 | | |
| WO | 2013/126375 A1 | 8/2013 | | |
| WO | WO-2013126375 A1 * | 8/2013 | ............. | C07C 51/09 |
| WO | 2014/004858 A1 | 1/2014 | | |
| WO | 2014/008232 A2 | 1/2014 | | |
| WO | 2015/085295 A2 | 6/2015 | | |
| WO | 2015/138975 A1 | 9/2015 | | |
| WO | 2015/171372 A1 | 11/2015 | | |
| WO | 2015/184289 A1 | 12/2015 | | |
| WO | 2016/015019 A1 | 1/2016 | | |
| WO | 2016/130947 A1 | 8/2016 | | |
| WO | 2016/130977 A1 | 8/2016 | | |
| WO | 2016/130988 A1 | 8/2016 | | |
| WO | 2016/130993 A1 | 8/2016 | | |
| WO | 2016/130998 A1 | 8/2016 | | |
| WO | 2016/131001 A1 | 8/2016 | | |
| WO | 2016/131003 A1 | 8/2016 | | |
| WO | 2016/131004 A1 | 8/2016 | | |
| WO | WO-2017023777 A1 | 2/2017 | | |
| WO | WO-2017023820 A1 | 2/2017 | | |
| WO | 2017/165344 A1 | 9/2017 | | |
| WO | 2017/165345 A1 | 9/2017 | | |
| WO | WO-2018085251 A1 | 5/2018 | | |
| WO | WO-2018085254 A1 | 5/2018 | | |
| WO | WO-2018136638 A1 | 7/2018 | | |
| WO | WO-2018170006 A1 | 9/2018 | | |

OTHER PUBLICATIONS

Billingham et al., "Polymerization and Copolymerizationof β-Butyrolactone by Aluminium Compounds", Journal of Organometallic Chemistry, vol. 341, No. 1-3, 1988, pp. 83-89.
Church et al., "Carbonylation of Heterocycles by Homogeneous Catalysts", Chemical Communication, 2007, pp. 657-674.
Getzler et al., "Synthesis of β-Lactones: A Highly Active and Selective Catalyst for Epoxide Carbonylation", Journal of the American Chemical Society. vol. 124, No. 7, 2002, pp. 1174-1175.
Gross et al., "Polymerization of .Beta.-Monosubstituted-.Beta.-Propiolactones using Trialkylaluminum-Water Catalytic Systems and Polymer Characterization", Macromolecules, vol. 21, No. 9, 1988, pp. 2657-2668.
Hori et al., "Ring-Opening Polymerization of Pptically Active .Beta.-Butyrolactone using Distannoxane Catalysts: Synthesis of High-Molecular-Weight Poly (3-Hydroxybutyrate)", Macromolecules, vol. 26, No. 20, 1993, pp. 5533-5534.
International Search Report and Written Opinion received for PCT Application No. PCT/US2016/017844, dated May 6, 2016, 10 Pages.
International Preliminary Report on Patentability received for PCT Patent Application No. PCT/US2016/017844, dated Aug. 24, 2017, 7 pages.
Rieth et al., "Single-Site β-Diiminate Zinc Catalysts for the Ring-Opening Polymerization of β-Butyrolactone and β-Valerolactone to Poly(3-hydroxyalkanoates)", Journal of the American Chemical Society, vol. 124, No. 51, 2002, pp. 15239-15248.
Schechtman et al, "Chemical Synthesis of Isotactic Poly(3-Hydroxyalkanoates)", Polymer Preprints, Division of Polymer Chemistry, Inc., vol. 40, No. 1, 1999, pp. 508-509.

(56) References Cited

OTHER PUBLICATIONS

Tanahashi et al., "Thermal Properties and Stereoregularity of Poly (3-Hydroxybutyrate) prepared from Optically Active .Beta.-Butyrolactone with a Zinc-based Catalyst", Macromolecules, vol. 24, No. 20, 1991, pp. 5732-5733.

Zhang et al., "Stereochemistry of the Ring-Opening Polymerization of (S)-β-Butyrolactone", Macromolecules, vol. 23, No. 13, 1990, pp. 3206-3212.

Extended European Search Report (includes Supplementary European Search Report and European Search Opinion) received for European Patent Application No. 16750004.0, dated Sep. 6, 2018, 6 pages.

\* cited by examiner

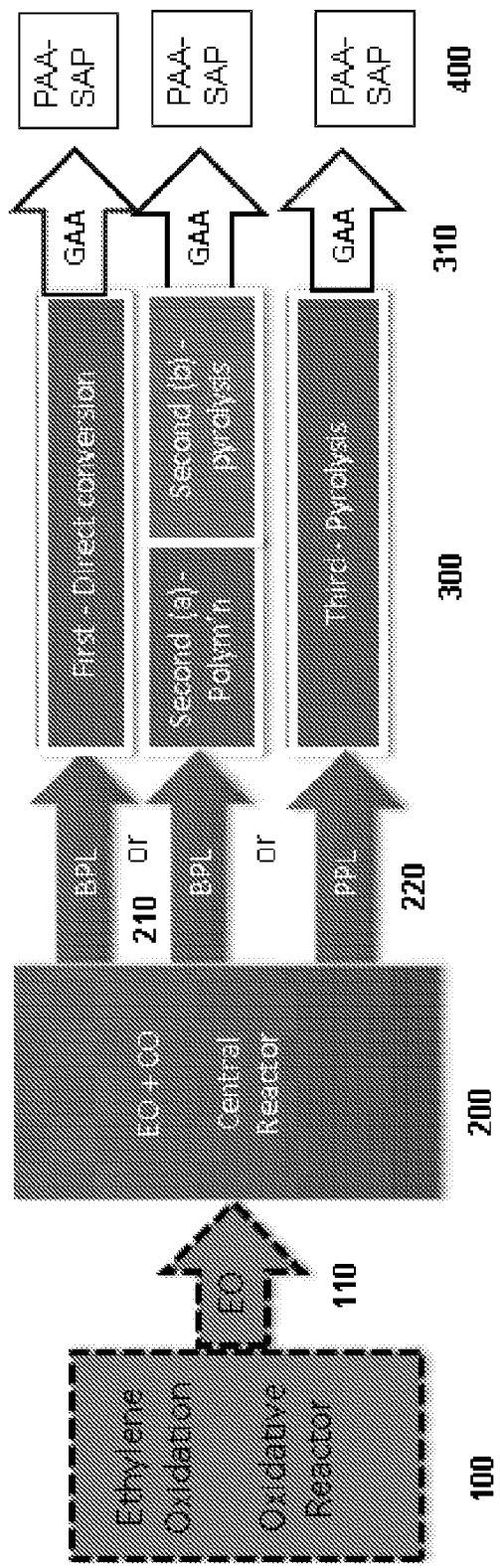

SYSTEMS AND PROCESSES FOR POLYACRYLIC ACID PRODUCTION

CROSS-REFERENCE TO RELATED APPLICATIONS

This application is a U.S. national phase patent application of PCT/US2016/017844, filed Feb. 12, 2016, which claims priority to and the benefit of U.S. Provisional Patent Application No. 62/116,229, filed Feb. 13, 2015, each of which is incorporated herein by reference in its entirety.

FIELD

The present disclosure relates generally to the production of polyacrylic acid, and more specifically to the production of polyacrylic acid from ethylene.

BACKGROUND

Methods have been described where acrylic acid (AA) is produced via the pyrolysis of polypropiolactone (PPL) (e.g., see U.S. Pat. No. 2,361,036). However, PPL pyrolysis as described in this and related literature does not produce acrylic acid of sufficient purity for direct use in radical polymerization for superabsorbent polymer (SAP) production. Instead, the methods require expensive and energy intensive purification of the acrylic acid before it can be polymerized to produce SAP. There is therefore a need in the art for methods of directly producing glacial acrylic without the need for expensive and energy intensive AA purification.

Glacial acrylic acid, a purified form of acrylic acid, can be used to make polyacrylic acid for superabsorbent polymers (SAPs). At least two problems currently known in the art hamper the production and/or purification of glacial acrylic acid.

First, acrylic acid is primarily produced via vapor phase oxidation of propylene via an acrolein aldehyde intermediate. Products of propylene oxidation, such as the acrolein aldehyde, and by-products of propylene oxidation, such as other aldehyde impurities, are difficult and expensive to remove from crude acrylic acid. Aldehyde impurities hinder polymerization to polyacrylic acid and discolor this polymer.

Second, acrylic acid is extremely reactive and susceptible to unwanted Michael addition and free-radical polymerization with itself. Therefore, even after glacial acrylic acid is purified, it gradually degrades unless stabilizers, such as radical polymerization inhibitors, are added to retard unwanted side reactions. Stabilizers, however, are expensive and may interfere with the conversion of acrylic acid to polyacrylic acid.

Thus, there is a need in the art for methods to produce acrylic acid, including glacial acrylic acid, on a commercial scale.

BRIEF SUMMARY

The systems and processes described herein directly produce acrylic acid (including glacial acrylic acid), and provide solutions to problems known in the art related to the production of acrylic acid. Described herein are systems and methods for producing polyacrylic acid (PAA) from ethylene, rather than propylene, that eliminate products and byproducts of propylene oxidation. Because the disclosed methods are conducted within the single integrated system described below, highly reactive intermediates, including ethylene oxide (EO), beta propiolactone (BPL), and acrylic acid (AA) are swiftly carried through to the relatively stable polyacrylic acid (PAA). The disclosed systems and methods can be used to efficiently prepare PAA and SAPs of excellent purity.

Also described are systems and methods for the production of polyacrylic acid and superabsorbent polymers from ethylene. Further described are systems and methods to prepare superabsorbent polymers from the ethylene-derived polyacrylic acid.

In one aspect, a system is provided for the production of polyacrylic acid (PAA) from ethylene, within an integrated system, comprising:
  an oxidative reactor, comprising an inlet fed by ethylene, an oxidative reaction zone that converts at least some of the ethylene to ethylene oxide (EO), and an outlet which provides an outlet stream comprising the EO,
  a central reactor, comprising an inlet fed by an EO source, and a carbon monoxide (CO) source, a central reaction zone that converts at least some of the EO to beta propiolactone (BPL) or polypropiolactone (PPL), and an outlet which provides an outlet stream comprising the BPL or PPL,
  one or more of (i), (ii) and (iii):
    (i) a first reactor, comprising an inlet fed by the outlet stream comprising BPL of the central reactor, a first reaction zone that converts at least some of the BPL to AA, and an outlet which provides an outlet stream comprising the AA,
    (ii) a second (a) reactor, comprising an inlet fed by the outlet stream comprising BPL of the central reactor, a second (a) reaction zone that converts at least some of the BPL to PPL, and an outlet which provides an outlet stream comprising the PPL, and a second (b) reactor, comprising an inlet fed by the outlet stream comprising PPL of the second (a) reactor, a second (b) reaction zone that converts at least some of the PPL to AA, and an outlet which provides an outlet stream comprising the AA, and
    (iii) a third reactor, comprising an inlet fed by the outlet stream comprising PPL of the central reactor, a third reaction zone that converts at least some of the PPL to a third product, and an outlet which provides an outlet stream comprising the AA, and
    (iv) a fourth reactor, comprising an inlet fed by the outlet stream comprising AA of one or more of the first, second (b) and third reactor, a fourth reaction zone that converts at least some of the AA to polyacrylic acid (PAA), or a salt thereof, and an outlet which provides an outlet stream comprising the PAA, or a salt thereof, and
  a controller for independently modulating production of the EO, BPL, PPL, AA and PAA.

In one variation, provided is an integrated system for producing polyacrylic acid (PAA) from ethylene, comprising:
  an oxidative reactor, comprising:
    an inlet configured to receive ethylene,
    an oxidative reaction zone configured to convert at least some of the ethylene to ethylene oxide (EO), and
    an outlet configured to provide an EO stream comprising the EO;
  a central reactor, comprising:
    an inlet configured to receive EO from the EO stream of the oxidative reactor, and carbon monoxide (CO) from a CO source, a central reaction zone configured to convert at least some of the EO to beta propiolactone (BPL) or polypropiolactone (PPL), or a combination thereof, and an outlet configured to provide a carbonylation stream comprising the BPL, or a carbonylation stream comprising the PPL, or a combination thereof;

one or more of (i), (ii) and (iii):

(i) a first reactor, comprising:
an inlet configured to receive BPL from the carbonylation stream of the central reactor,
a first reaction zone configured to convert at least some of the BPL to AA, and
an outlet configured to provide an AA stream comprising the AA, (ii) a second (a) reactor, comprising:
an inlet configured to receive BPL from the carbonylation stream of the central reactor,
a second (a) reaction zone configured to convert at least some of the BPL to PPL, and
an outlet configured to provide a PPL stream comprising the PPL, and
a second (b) reactor, comprising:
an inlet configured to receive the PPL stream of the second (a) reactor,
a second (b) reaction zone configured to convert at least some of the PPL to AA, and
an outlet configured to provide an AA stream comprising the AA, and (iii) a third reactor, comprising:
an inlet configured to receive PPL from the carbonylation stream of the central reactor,
a third reaction zone configured to convert at least some of the PPL to AA, and
an outlet configured to provide an AA stream comprising the AA;

a fourth reactor, comprising:
an inlet configured to receive the AA stream of one or more of the first, second (b) and third reactor,
a fourth reaction zone configured to convert at least some of the AA to polyacrylic acid (PAA), or a salt thereof, and
an outlet configured to provide a PAA stream comprising the PAA, or a salt thereof; and a controller to independently modulate production of the EO, BPL, PPL, AA and PAA.

In certain embodiments, the system further comprises a SAP reactor configured to receive the PAA stream, and to convert at least some of the PAA in the PAA stream to a SAP.

In some aspects, provided is a method for converting ethylene to polyacrylic acid (PAA) within an integrated system, the method comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to beta propiolactone (BPL) or polypropiolactone (PPL), or a combination thereof, in the central reaction zone to produce a carbonylation stream comprising BPL, or a carbonylation stream comprising PPL, or a combination thereof;

(i) directing the carbonylation stream comprising BPL to an AA reactor, and converting at least some of the BPL in the carbonylation stream to AA in the AA reactor to produce an AA stream comprising the AA; or (ii) directing the carbonylation stream comprising BPL to a PPL reactor, converting at least some of the BPL in the carbonylation stream to PPL in the PPL reactor to produce a PPL stream comprising PPL, directing the PPL stream to an AA reactor (also referred to in FIG. 1 as second (b) reactor), and converting at least some of the PPL to AA in the AA reactor to produce an AA stream; or (iii) directing the carbonylation stream comprising PPL to an AA reactor, and converting at least some of the PPL in the carbonylation stream to AA in the AA reactor to produce an AA stream comprising AA; or any combinations of (i)-(iii) above;

directing the AA streams of (i)-(iii) above to a PAA reactor; and converting at least a portion of the AA of the AA streams of (i)-(iii) above to polyacrylic acid (PAA), or a salt thereof, in the PAA reactor.

In another aspect, related methods are disclosed for the production of SAPs and PAA from ethylene.

Provided in another aspect is an article, such as a disposable diaper, comprising any of the SAPs described herein. The disclosed systems, methods and articles are described in greater detail below.

BRIEF DESCRIPTION OF THE FIGURES

The present application can be best understood by reference to the following description taken in conjunction with the accompanying FIGURE, in which like parts may be referred to by like numerals.

FIG. 1 shows, in one embodiment, an exemplary process schematic for the disclosed methods and systems.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In some variations, the aliphatic group is unbranched or branched. In other variations, the aliphatic group is cyclic. Unless otherwise specified, in some variations, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In certain embodiments, aliphatic groups contain 1-5 carbon atoms, In certain embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, for example, linear or branched, alkyl, alkenyl, and alkynyl groups, and hybrids thereof such as (cycloalkyl) alkyl, (cycloalkenyl)alkyl or (cycloalkyl)alkenyl.

The term "heteroaliphatic" as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups. In some variations, the heteroaliphatic group is branched or unbranched. In other variations, the heteroaliphatic group is cyclic. In yet other variations, the heteroaliphatic group is acyclic.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, for example, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In certain embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, a carbocyclic group is bicyclic. In certain embodiments, a carbocyclic group is tricyclic. In certain embodiments, a carbocyclic group is polycyclic.

The term "alkyl," as used herein, refers to a saturated hydrocarbon radical. In some variations, the alkyl group is a saturated, straight- or branched-chain hydrocarbon radicals derived from an aliphatic moiety containing between one and six carbon atoms by removal of a single hydrogen atom. Unless otherwise specified, in some variations, alkyl groups contain 1-12 carbon atoms. In certain embodiments, alkyl groups contain 1-8 carbon atoms. In certain embodiments, alkyl groups contain 1-6 carbon atoms. In certain embodiments, alkyl groups contain 1-5 carbon atoms, In certain embodiments, alkyl groups contain 1-4 carbon atoms, in yet other embodiments alkyl groups contain 1-3 carbon atoms, and in yet other embodiments alkyl groups contain 1-2 carbon atoms. Alkyl radicals may include, for example, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, and dodecyl.

The terms "alkene" and "alkenyl," as used herein, denote a monovalent group having at least one carbon-carbon double bond. In some variations, the alkenyl group is a monovalent group derived from a straight- or branched-chain aliphatic moiety having at least one carbon-carbon double bond by the removal of a single hydrogen atom. Unless otherwise specified, in some variations, alkenyl groups contain 2-12 carbon atoms. In certain embodiments, alkenyl groups contain 2-8 carbon atoms. In certain embodiments, alkenyl groups contain 2-6 carbon atoms. In certain embodiments, alkenyl groups contain 2-5 carbon atoms, In certain embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, and 1-methyl-2-buten-1-yl.

The term "alkynyl," as used herein, refers to a monovalent group having at least one carbon-carbon triple bond. In some variations, the alkynyl group is a monovalent group derived from a straight- or branched-chain aliphatic moiety having at least one carbon-carbon triple bond by the removal of a single hydrogen atom. Unless otherwise specified, in some variations, alkynyl groups contain 2-12 carbon atoms. In certain embodiments, alkynyl groups contain 2-8 carbon atoms. In certain embodiments, alkynyl groups contain 2-6 carbon atoms. In certain embodiments, alkynyl groups contain 2-5 carbon atoms, In certain embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, for example, ethynyl, 2-propynyl (propargyl), and 1-propynyl.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include, for example, cyclopropane, cyclobutane, cyclopentane, cyclohexane, bicyclo[2,2,1]heptane, norbornene, phenyl, cyclohexene, naphthalene, and spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments, "aryl" refers to an aromatic ring system which includes, for example, phenyl, naphthyl, and anthracyl, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, and tetrahydronaphthyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 pi ($\pi$) electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-" as used herein, also include groups in which a heteroaromatic ring is fused to one or more aryl, cycloaliphatic, or heterocyclyl rings, where the radical or point of attachment is on the heteroaromatic ring. Examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and may be saturated or partially unsaturated, and have, in addition to carbon atoms, one or more, preferably one to four, heteroatoms, as defined above. In some variations, the heterocyclic group is a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, for example, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds described herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned herein are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$; —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-4}$C(O)N(R$^\circ$)$_2$; —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "reaction zone" refers to a reactor or portion thereof where a particular reaction occurs. A given reaction may occur in multiple reaction zones, and different reaction zones may comprise separate reactors or portions of the same reactor. A "reactor" typically comprises one or more vessels with one or more connections to other reactors or system components.

As used herein, the terms "reaction stream" and "inlet stream" refer to a solid, liquid or gas medium comprising a reactant that enters a reaction zone. As used herein, the terms "product stream" and "outlet stream" refer to a solid, liquid or gas medium comprising a product that exits a reaction zone. Each reaction and product (referring to inlet or outlet, respectively) stream may be neat with respect to reactant and product or they may include co-reactants, co-products, catalysts, solvents, carrier gas and/or impurities.

The term "polymer", as used herein, refers to a molecule comprising multiple repeating units. In some variations, the polymer is a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer may be a copolymer, terpolymer, heteropolymer, block copolymer, or tapered heteropolymer of one or more epoxides. In one variation, the polymer may be a copolymer, terpolymer, heteropolymer, block copolymer, or tapered heteropolymer of two or more monomers.

In some variations, the term "glycidyl", as used herein, refers to an oxirane substituted with a hydroxyl methyl group or a derivative thereof. In other variations, the term glycidyl as used herein is meant to include moieties having additional substitution on one or more of the carbon atoms of the oxirane ring or on the methylene group of the hydroxymethyl moiety, examples of such substitution may include, for example, alkyl groups, halogen atoms, and aryl groups. The terms glycidyl ester, glycidyl acrylate, glydidyl ether etc. denote substitution at the oxygen atom of the above-mentioned hydroxymethyl group, e.g., that oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Acrylates may include, for example, acrylate, methacrylate, ethacrylate, cinnamate (3-phenylacrylate), crotonate, tiglate, and senecioate.

As used herein, the terms "crude acrylic acid" and "glacial acrylic acid" (GAA) describe AA of relatively low and high purity, respectively. Crude AA (also called technical grade AA) has a typical minimum overall purity level of 94%, by weight, and can be used to make acrylic esters for paint, adhesive, textile, paper, leather, fiber, and plastic additive applications. GAA has a typical overall purity level ranging from 98% to 99.99% and can be used to make polyacrylic acid (PAA), or a salt thereof, for superabsorbent polymers (SAPs) in disposable diapers, training pants, adult incontinence undergarments and sanitary napkins. PAA, or a salt thereof, is also used in compositions for paper and water treatment, and in detergent co-builder applications. In some variations, acrylic acid has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

Suitable salts of PAA include metal salts, such those of any alkali (e.g., Na$^+$, K$^+$) cations, alkaline earth cations. In certain embodiments, the PAA salt is the Na⁺ salt, i.e., sodium PAA. In certain embodiments, the salt is the K⁺ salt, i.e., potassium PAA.

Impurities in GAA are reduced to an extent possible to facilitate a high-degree of polymerization to PAA, or a salt thereof, and avoid adverse effects from side products in end applications. For example, aldehyde impurities in AA hinder polymerization and may discolor the PAA. Maleic anhydride impurities form undesirable copolymers which may be detrimental to polymer properties. Carboxylic acids, e.g., saturated carboxylic acids that do not participate in the polymerization, can affect the final odor of PAA, or a salt thereof, or SAP-containing products and/or detract from their use. For example, foul odors may emanate from SAP that contains acetic acid or propionic acid and skin irritation may result from SAP that contains formic acid.

The reduction or removal of impurities from petroleum-based AA is costly, whether to produce petroleum-based crude AA or petroleum-based glacial AA. Costly multistage distillations and/or extraction and/or crystallizations steps are generally employed (e.g., as described in U.S. Pat. Nos. 5,705,688 and 6,541,665). Notable impurities from petroleum-based AA that are reduced and/or eliminated from the disclosed compositions include, for example, aldehyde impurities and products or byproducts of propylene oxidation.

As used herein, the term "product or byproduct of propylene oxidation" or "compound that derives from the oxidation of propylene" are used interchangeably to refer to products and byproducts of propylene oxidation including, for example, $C_1$ compounds such as formaldehyde, and formic acid; $C_2$ compounds such as acetaldehyde, acetic acid; $C_3$ compounds such as propylene, allyl alcohol, acrolein (i.e., propenal), propanol, isopropyl alcohol, acetone, propionic acid; $C_4$ compounds such as maleic anhydride; and $C_5$ compounds such as furfural, etc.

As used herein, the term "aldehyde impurity" includes any of the aldehydes in the preceding paragraph.

As used herein, the term "substantially free" means, in some variations, less than 5 wt %, 1 wt %, 0.1 wt %, 0.01 wt %, or a range including any two of these values, or less than 10,000 ppm, 1,000 ppm, 500 ppm, 100 ppm, 50 ppm, 10 ppm, or a range including any two of these values. In one variation, a composition that is substantially free of Compound A has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of Compound A.

Stabilizers are commonly used to preserve AA. As used herein, the term "stabilizer" includes any radical polymerization inhibitor or an anti-foaming agent. AA is susceptible to unwanted Michael addition to itself and to unwanted free-radical polymerization with itself, which may be counteracted by addition of polymerization inhibitors to the AA. Suitable polymerization inhibitors include, for example, hydroquinone monomethyl ether, MEHQ, alkylphenols, such as o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol and 2-methyl-4-tert-butylphenol and hydroxyphenols such as hydroquinone, catechol, resorcinol, 2-methylhydroquinone and 2,5-di-tert-butylhydroquinone. Examples of anti-foaming agents include silicones (e.g., polydimethylsiloxanes), alcohols, stearates, and glycols.

As used herein, the term "about" preceding one or more numerical values means the numerical value ±5%. It should be understood that reference to "about" a value or parameter herein includes (and describes) embodiments that are directed to that value or parameter per se. For example, description referring to "about x" includes description of "x" per se.

DETAILED DESCRIPTION

Described herein are systems and methods for producing polyacrylic acid (PAA) from ethylene, rather than propylene, that eliminate products and byproducts of propylene oxidation. Also, because the disclosed systems and methods are conducted with a single integrated system, highly reactive intermediates, including ethylene oxide (EO), beta propiolactone (BPL), and acrylic acid are swiftly carried through to the relatively stable polyacrylic acid (PAA). The disclosed systems and methods can be used to prepare PAA and SAPs of excellent (e.g., high) purity.

Systems

Provided herein are systems for producing PAA and/or SAP from ethylene within an integrated system. In one aspect, a system is provided for the production of polyacrylic acid (PAA) from ethylene, within an integrated system, comprising:
an oxidative reactor, comprising an inlet fed by ethylene, an oxidative reaction zone that converts at least some of the ethylene to ethylene oxide (EO), and an outlet which provides an outlet stream comprising the EO,
a central reactor, comprising an inlet fed by an EO source, and a carbon monoxide (CO) source, a central reaction zone that converts at least some of the EO to beta propiolactone (BPL) or polypropiolactone (PPL), and an outlet which provides an outlet stream comprising the BPL or PPL,
one or more of (i), (ii) and (iii):
 (i) a first reactor, comprising an inlet fed by the outlet stream comprising BPL of the central reactor, a first reaction zone that converts at least some of the BPL to AA, and an outlet which provides an outlet stream comprising the AA,
 (ii) a second (a) reactor, comprising an inlet fed by the outlet stream comprising BPL of the central reactor, a second (a) reaction zone that converts at least some of the BPL to PPL, and an outlet which provides an outlet stream comprising the PPL, and a second (b) reactor, comprising an inlet fed by the outlet stream comprising PPL of the second (a) reactor, a second (b) reaction zone that converts at least some of the PPL to AA, and an outlet which provides an outlet stream comprising the AA, and
 (iii) a third reactor, comprising an inlet fed by the outlet stream comprising PPL of the central reactor, a third reaction zone that converts at least some of the PPL to a third product, and an outlet which provides an outlet stream comprising the AA, and
 (iv) a fourth reactor, comprising an inlet fed by the outlet stream comprising AA of one or more of the first, second (b) and third reactor, a fourth reaction zone that converts at least some of the AA to polyacrylic acid (PAA), or a salt thereof, and an outlet which provides an outlet stream comprising the PAA, or a salt thereof, and a controller for independently modulating production of the EO, BPL, PPL, AA and PAA.

In some variations, provided is a system for producing polyacrylic acid (PAA) from ethylene, comprising:
an oxidative reactor, comprising:
an inlet configured to receive ethylene,
an oxidative reaction zone configured to convert at least some of the ethylene to ethylene oxide (EO), and
an outlet configured to provide an EO stream comprising the EO;
a central reactor, comprising:
an inlet configured to receive EO from the EO stream of the oxidative reactor, and carbon monoxide (CO) from a CO source,
a central reaction zone configured to convert at least some of the EO to beta propiolactone (BPL) or polypropiolactone (PPL), or a combination thereof, and
an outlet configured to provide a carbonylation stream comprising the BPL, or a carbonylation stream comprising the PPL, or a combination thereof;
one or more of (i), (ii) and (iii):
(i) a first reactor, comprising:
an inlet configured to receive BPL from the carbonylation stream of the central reactor,
a first reaction zone configured to convert at least some of the BPL to AA, and
an outlet configured to provide an AA stream comprising the AA,
(ii) a second (a) reactor, comprising:
an inlet configured to receive BPL from the carbonylation stream of the central reactor,
a second (a) reaction zone configured to convert at least some of the BPL to PPL, and
an outlet configured to provide a PPL stream comprising the PPL, and
a second (b) reactor, comprising:
an inlet configured to receive the PPL stream of the second (a) reactor,
a second (b) reaction zone configured to convert at least some of the PPL to AA, and
an outlet configured to provide an AA stream comprising the AA, and
(iii) a third reactor, comprising:
an inlet configured to receive PPL from carbonylation stream of the central reactor,
a third reaction zone configured to convert at least some of the PPL to AA, and
an outlet configured to provide an AA stream comprising the AA;
a fourth reactor, comprising:
an inlet configured to receive the AA stream of one or more of the first, second (b) and third reactor,
a fourth reaction zone configured to convert at least some of the AA to polyacrylic acid (PAA), or a salt thereof, and
an outlet configured to provide a PAA stream comprising the PAA, or a salt thereof; and
a controller to independently modulate production of the EO, BPL, PPL, AA and PAA.

In one embodiment, the system comprises (i). Thus, in one variation, provided is a system for producing polyacrylic acid (PAA) from ethylene, within an integrated system, comprising:
an oxidative reactor, comprising:
an inlet configured to receive ethylene,
an oxidative reaction zone configured to convert at least some of the ethylene to ethylene oxide (EO), and
an outlet configured to provide an EO stream comprising the EO;
a central reactor, comprising:
an inlet configured to receive EO from the EO stream of the oxidative reactor, and carbon monoxide (CO) from a CO source,
a central reaction zone configured to convert at least some of the EO to beta propiolactone (BPL) or polypropiolactone (PPL), or a combination thereof, and
an outlet configured to provide a carbonylation stream comprising the BPL;
an acrylic acid (AA) reactor (also referred to in FIG. 1 as first reactor), comprising:
an inlet configured to receive BPL from the carbonylation stream of the central reactor,
a reaction zone configured to convert at least some of the BPL to AA, and
an outlet configured to provide an AA stream comprising the AA,
a PAA reactor, comprising:
an inlet configured to receive AA from the AA stream of the AA reactor,
a reaction zone configured to convert at least some of the AA to polyacrylic acid (PAA), or a salt thereof, and
an outlet configured to provide a PAA stream comprising the PAA, or a salt thereof; and
a controller to independently modulate production of the EO, BPL, AA and PAA.

In another embodiment, the system comprises (ii). Thus, in one variation, provided is a system for producing polyacrylic acid (PAA) from ethylene, within an integrated system, comprising:
an oxidative reactor, comprising:
an inlet configured to receive ethylene,
an oxidative reaction zone configured to convert at least some of the ethylene to ethylene oxide (EO), and
an outlet configured to provide an EO stream comprising the EO;
a central reactor, comprising:
an inlet configured to receive EO from the EO stream of the oxidative reactor, and carbon monoxide (CO) from a CO source,
a central reaction zone configured to convert at least some of the EO to beta propiolactone (BPL) or polypropiolactone (PPL), or a combination thereof, and
an outlet configured to provide a carbonylation stream comprising the BPL;
a PPL reactor (also referred to in FIG. 1 as second (a) reactor), comprising:
an inlet configured to receive BPL from the carbonylation stream of the central reactor,
a reaction zone configured to convert at least some of the BPL to PPL, and
an outlet configured to provide a PPL stream comprising the PPL;
an AA reactor (also referred to in FIG. 1 as second (b) reactor), comprising:
an inlet configured to receive the PPL stream,
a reaction zone configured to convert at least some of the PPL to AA, and
an outlet configured to provide an AA stream comprising the AA;

a PAA reactor, comprising:
  an inlet configured to receive AA from the AA stream of the AA reactor,
  a reaction zone configured to convert at least some of the AA to polyacrylic acid (PAA), or a salt thereof, and
  an outlet configured to provide a PAA stream comprising the PAA, or a salt thereof; and
a controller to independently modulate production of the EO, BPL, AA and PAA.

In another embodiment, the system comprises (iii). Thus, in another variation, provided is a system for producing polyacrylic acid (PAA) from ethylene, within an integrated system, comprising:
  an oxidative reactor, comprising:
    an inlet configured to receive ethylene,
    an oxidative reaction zone configured to convert at least some of the ethylene to ethylene oxide (EO), and
    an outlet configured to provide an EO stream comprising the EO;
  a central reactor, comprising:
    an inlet configured to receive EO from the EO stream of the oxidative reactor, and carbon monoxide (CO) from a CO source,
    a central reaction zone configured to convert at least some of the EO to beta propiolactone (BPL) or polypropiolactone (PPL), or a combination thereof, and
    an outlet configured to provide a carbonylation stream comprising the PPL;
  an AA reactor (also referred to in FIG. 1 as third reactor), comprising:
    an inlet configured to receive PPL from the carbonylation stream of the central reactor,
    a reaction zone configured to convert at least some of the PPL to AA, and an outlet configured to provide an AA stream comprising the AA;
  a PAA reactor, comprising:
    an inlet configured to receive AA from the AA stream of the AA reactor,
    a reaction zone configured to convert at least some of the AA to polyacrylic acid (PAA), or a salt thereof, and
    an outlet configured to provide a PAA stream comprising the PAA, or a salt thereof; and
  a controller to independently modulate production of the EO, PPL, AA and PAA.

In certain embodiments, the system comprises two of (i), (ii) and (iii). For example, in one embodiment, the system comprises (i) and (iii). Thus, in one variation, provided is a system for producing polyacrylic acid (PAA) from ethylene, within an integrated system, comprising:
  an oxidative reactor, comprising:
    an inlet configured to receive ethylene,
    an oxidative reaction zone configured to convert at least some of the ethylene to ethylene oxide (EO), and
    an outlet configured to provide an EO stream comprising the EO;
  a central reactor, comprising:
    an inlet configured to receive EO from the EO stream of the oxidative reactor, and carbon monoxide (CO) from a CO source,
    a central reaction zone configured to convert at least some of the EO to beta propiolactone (BPL) and polypropiolactone (PPL), and
    an outlet configured to provide a first carbonylation stream comprising the BPL, and a second carbonylation stream comprising the PPL;
  a first AA reactor (also referred to in FIG. 1 as first reactor), comprising:
    an inlet configured to receive BPL from the first carbonylation stream of the central reactor,
    a reaction zone configured to convert at least some of the BPL to AA, and
    an outlet configured to provide a first AA stream comprising the AA;
  a second AA reactor (also referred to in FIG. 1 as third reactor), comprising:
    an inlet configured to receive PPL from the second carbonylation stream of the central reactor,
    a reaction zone configured to convert at least some of the PPL to AA, and
    an outlet configured to provide a second AA stream comprising the AA;
  a PAA reactor, comprising:
    at least one inlet configured to receive AA from one or both of the first AA stream and the second AA stream,
    a reaction zone configured to convert at least some of the AA to polyacrylic acid (PAA), or a salt thereof, and
    an outlet configured to provide a PAA stream comprising the PAA, or a salt thereof; and
  a controller to independently modulate production of the EO, BPL, PPL, AA and PAA.

In another embodiment, the system comprises (ii) and (iii). Thus, in another variation, provided is a system for producing polyacrylic acid (PAA) from ethylene, within an integrated system, comprising:
  an oxidative reactor, comprising:
    an inlet configured to receive ethylene,
    an oxidative reaction zone configured to convert at least some of the ethylene to ethylene oxide (EO), and
    an outlet configured to provide an EO stream comprising the EO;
  a central reactor, comprising:
    an inlet configured to receive EO from the EO stream of the oxidative reactor, and carbon monoxide (CO) from a CO source,
    a central reaction zone configured to convert at least some of the EO to beta propiolactone (BPL) and polypropiolactone (PPL), and
    an outlet configured to provide a first carbonylation stream comprising the BPL, and a second carbonylation stream comprising the PPL;
  a PPL reactor (also referred to in FIG. 1 as second (a) reactor), comprising:
    an inlet configured to receive BPL from the first carbonylation stream of the central reactor,
    a reaction zone configured to convert at least some of the BPL to PPL, and
    an outlet configured to provide a PPL stream comprising the PPL;
  a first AA reactor (also referred to in FIG. 1 as second (b) reactor), comprising:
    an inlet configured to receive PPL from the PPL stream of the PPL reactor,
    a reaction zone configured to convert at least some of the PPL to AA, and
    an outlet configured to provide a first AA stream comprising the AA;

a second AA reactor (also referred to in FIG. 1 as third reactor), comprising:
  an inlet configured to receive PPL from the second carbonylation stream of the central reactor,
  a reaction zone configured to convert at least some of the PPL to AA, and
  an outlet configured to provide a second AA stream comprising the AA;
a PAA reactor, comprising:
  at least one inlet configured to receive AA from one or both of the first AA stream and the second AA stream,
  a reaction zone configured to convert at least some of the AA to polyacrylic acid (PAA), or a salt thereof, and
  an outlet configured to provide a PAA stream comprising the PAA, or a salt thereof; and
a controller to independently modulate production of the EO, BPL, PPL, AA and PAA.

In some variations of the foregoing system, the first and second AA reactors may be the same reactor. In other variations, the first and second reactors are separate reactors.

In another embodiment, the system comprises (i) and (ii). Thus, in yet another variation, provided is a system for producing polyacrylic acid (PAA) from ethylene, within an integrated system, comprising:
an oxidative reactor, comprising:
  an inlet configured to receive ethylene,
  an oxidative reaction zone configured to convert at least some of the ethylene to ethylene oxide (EO), and
  an outlet configured to provide an EO stream comprising the EO;
a central reactor, comprising:
  an inlet configured to receive EO from the EO stream of the oxidative reactor, and carbon monoxide (CO) from a CO source,
  a central reaction zone configured to convert at least some of the EO to beta propiolactone (BPL), and
  an outlet configured to provide a BPL stream comprising the BPL;
a first AA reactor (also referred to in FIG. 1 as first reactor), comprising:
  an inlet configured to receive at least a portion of the BPL stream,
  a reaction zone configured to convert at least some of the BPL to AA, and
  an outlet configured to provide a first AA stream comprising the AA;
a PPL reactor (also referred to in FIG. 1 as second (a) reactor), comprising:
  an inlet configured to receive at least a portion of the BPL stream,
  a reaction zone configured to convert at least some of the BPL to PPL, and
  an outlet configured to provide a PPL stream comprising the PPL;
a second AA reactor (also referred to in FIG. 1 as second (b) reactor), comprising:
  an inlet configured to receive PPL from the PPL stream,
  a reaction zone configured to convert at least some of the PPL to AA, and
  an outlet configured to provide a second AA stream comprising the AA;
a PAA reactor, comprising:
  at least one inlet configured to receive AA from one or both of the first AA stream and the second AA stream,
  a reaction zone configured to convert at least some of the AA to polyacrylic acid (PAA), or a salt thereof, and
  an outlet configured to provide a PAA stream comprising the PAA, or a salt thereof; and
a controller to independently modulate production of the EO, BPL, PPL, AA and PAA.

In some variations of the foregoing system, the first and second AA reactors may be the same reactor. In other variations, the first and second AA reactors are separate reactors.

In some variations of the foregoing system where the first and second AA reactors are separate, the PAA reactor is configured to receive AA from both of the AA streams. For example, AA from the first AA stream and AA from the second AA stream may be combined, and in some variations, this combination may occur either at the inlet of the PAA reactor or at a point prior to the PAA reactor inlet. In other variations, the PAA reactor is configured to receive AA exclusively from the first AA stream or exclusively from the second AA stream. In some variations the system includes provision to allow an operator to control the ratio of the AA provided from the first AA stream and AA provided from the second AA stream and to change the ratio over time.

In certain embodiments, the system comprises all of (i), (ii) and (iii). Thus, in one variation, provided is a system for producing polyacrylic acid (PAA) from ethylene, within an integrated system, comprising:
an oxidative reactor, comprising:
  an inlet configured to receive ethylene,
  an oxidative reaction zone configured to convert at least some of the ethylene to ethylene oxide (EO), and
  an outlet configured to provide an EO stream comprising the EO;
a central reactor, comprising:
  an inlet configured to receive EO from the EO stream of the oxidative reactor, and carbon monoxide (CO) from a CO source,
  a central reaction zone configured to convert at least some of the EO to beta propiolactone (BPL) and polypropiolactone (PPL), and
  an outlet configured to provide a first carbonylation stream comprising the BPL, and a second carbonylation stream comprising the PPL;
a first AA reactor (also referred to in FIG. 1 as the first reactor), comprising:
  an inlet configured to receive at least a portion of the first carbonylation stream of the central reactor,
  a reaction zone configured to convert at least some of the BPL to AA, and
  an outlet configured to provide a first AA stream comprising the AA;
a PPL reactor (also referred to in FIG. 1 as second (a) reactor), comprising:
  an inlet configured to receive at least a portion of the first carbonylation stream,
  a reaction zone configured to convert at least some of the BPL to PPL, and
  an outlet configured to provide a PPL stream comprising the PPL;
a second AA reactor (also referred to in FIG. 1 as second (b) reactor), comprising:
  an inlet configured to receive PPL from the PPL stream of the PPL reactor,
  a reaction zone configured to convert at least some of the PPL to AA, and an outlet configured to provide a second AA stream comprising the AA;

a third AA reactor (also referred to in FIG. 1 as third reactor), comprising:
an inlet configured to receive PPL from the second carbonylation stream of the central reactor,
a reaction zone configured to convert at least some of the PPL to AA, and
an outlet configured to provide a third AA stream comprising the AA;

a PAA reactor, comprising:
an inlet configured to receive AA from one or more of the first AA stream, the second AA stream, and the third AA stream,
a reaction zone configured to convert at least some of the AA to polyacrylic acid (PAA), or a salt thereof, and
an outlet configured to provide a PAA stream comprising the PAA, or a salt thereof; and a controller to independently modulate production of the EO, BPL, PPL, AA and PAA.

In some variations of the foregoing system, the first, second and third AA reactors may be the same reactor. In other variations, the first and second AA reactors may be the same, and the third AA reactor is a separate reactor. In yet other variations, the first, second and third reactors are all separate reactors.

In some variations of the foregoing system, the PAA reactor is configured to receive AA from all of the AA streams. For example, AA from the first AA stream AA from the second AA stream, and AA from the third AA stream may be combined, and in some variations, this combination may occur either at the inlet of the PAA reactor or at a point prior to the PAA reactor inlet. In other variations, the PAA reactor is configured to receive AA exclusively from the first AA stream, exclusively from the second AA stream, or exclusively from the third AA stream. In some variations the system includes provision to allow an operator to control the source of the AA provided to the PAA reactor and/or to control the ratio of AA supplied from the first AA stream, the second AA stream, and the third AA stream and to change source or the ratio of sources over time.

In some variations of the foregoing systems, the EO stream received by the central reactor may be the entire or partial EO stream from the oxidative reactor, and/or may be used directly from the oxidative reactor or be further treated prior to use in the oxidative reactor. For example, in one variation, the EO stream of the oxidative reactor may be further processed before it is fed into the central reactor. For example, in one variation, the EO stream of the oxidative reactor may be further dried and/or purified, prior to feeding into the central reactor. In other variations of the foregoing, the central reactor may receive a fraction of the EO stream provided by the oxidative reactor.

In certain embodiments, the systems described herein produce AA at about 200 to about 800 kilotons per annum (kta). In certain embodiments, the systems described herein can produce AA at about 200, 250, 300, 350, 400, 450, 500, 550, 600, 650, 700, 750, 800, 850, 900, 950, 1,000 kilotons per annum (kta), or within a range including any two of these values.

In certain embodiments, the AA produced by the systems is substantially free of an aldehyde impurity or a compound that derives from the oxidation of propylene. In some embodiments, the AA is substantially free of an aldehyde impurity. In some embodiments, the AA is substantially free of furfural. In some embodiments, the AA is substantially free of stabilizers. In some embodiments, the AA is substantially free of radical polymerization inhibitors. In some embodiments, the AA is substantially free of anti-foam agents.

In certain embodiments, the AA is glacial acrylic acid (GAA). In some variations, AA has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

In certain embodiments, the GAA is substantially free of an aldehyde impurity or a compound that derives from the oxidation of propylene. In some embodiments, the GAA is substantially free of an aldehyde impurity. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of an aldehyde impurity. In other variations, the AA stream has less than 10,000 ppm, 1,000 ppm, 500 ppm, 100 ppm, 50 ppm, 10 ppm, or a range including any two of the aforementioned values, of an aldehyde impurity.

In other variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of a compound that derives from the oxidation of propylene. In other variations, the AA stream has less than 10,000 ppm, 1,000 ppm, 500 ppm, 100 ppm, 50 ppm, 10 ppm, or a range including any two of the aforementioned values, of a compound that derives from the oxidation of propylene.

In some embodiments, the GAA is substantially free of furfural. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of furfural. In other variations, the AA stream has less than 10,000 ppm, 1,000 ppm, 500 ppm, 100 ppm, 50 ppm, 10 ppm, or a range including any two of the aforementioned values, of furfural.

In some embodiments, the GAA is substantially free of acetic acid. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of acetic acid. In other variations, the AA stream has less than 10,000 ppm, 1,000 ppm, 500 ppm, 100 ppm, 50 ppm, 10 ppm, or a range including any two of the aforementioned values, of acetic acid.

In some embodiments, the GAA is substantially free of stabilizers. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of stabilizers. In other variations, the AA stream has less than 10,000 ppm, 1,000 ppm, 500 ppm, 100 ppm, 50 ppm, 10 ppm, or a range including any two of the aforementioned values, of stabilizers.

In some embodiments, the GAA is substantially free of radical polymerization inhibitors. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of radical polymerization inhibitors. In other variations, the AA stream has less than 10,000 ppm, 1,000 ppm, 500 ppm, 100 ppm, 50 ppm, 10 ppm, or a range including any two of the aforementioned values, of radical polymerization inhibitors.

In some embodiments, the GAA is substantially free of anti-foam agents. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of anti-foam agents. In other variations, the AA stream has less than 10,000 ppm, 1,000 ppm, 500 ppm, 100 ppm, 50 ppm, 10 ppm, or a range including any two of the aforementioned values, of anti-foam agents.

In certain embodiments, the inlet to the fourth reactor (also referred to as the PAA reactor) is fed by one or more reactant streams comprising sodium hydroxide in the presence of a radical initiator to form a PAA sodium salt.

In certain embodiments, at least some of the AA is converted to the PAA, or a salt thereof, via gel polymerization, suspension polymerization or solution polymerization.

In certain embodiments, the PAA, or a salt thereof, is substantially free of an aldehyde impurity or a compound that derives from the oxidation of propylene. In some embodiments, the PAA is substantially free of an aldehyde impurity. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of an aldehyde impurity. In other variations, the PAA stream has less than 10,000 ppm, 1,000 ppm, 500 ppm, 100 ppm, 50 ppm, 10 ppm, or a range including any two of the aforementioned values, of an aldehyde impurity.

In other variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of a compound that derives from the oxidation of propylene. In other variations, the PAA stream has less than 10,000 ppm, 1,000 ppm, 500 ppm, 100 ppm, 50 ppm, 10 ppm, or a range including any two of the aforementioned values, of a compound that derives from the oxidation of propylene.

In some embodiments, the PAA is substantially free of furfural. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of furfural. In other variations, the PAA stream has less than 10,000 ppm, 1,000 ppm, 500 ppm, 100 ppm, 50 ppm, 10 ppm, or a range including any two of the aforementioned values, of furfural.

In some embodiments, the PAA is substantially free of acetic acid. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of acetic acid. In other variations, the PAA stream has less than 10,000 ppm, 1,000 ppm, 500 ppm, 100 ppm, 50 ppm, 10 ppm, or a range including any two of the aforementioned values, of acetic acid.

In some embodiments, the PAA is substantially free of stabilizers. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of stabilizers. In other variations, the PAA stream has less than 10,000 ppm, 1,000 ppm, 500 ppm, 100 ppm, 50 ppm, 10 ppm, or a range including any two of the aforementioned values, of stabilizers.

In some embodiments, the PAA is substantially free of radical polymerization inhibitors. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of radical polymerization inhibitors. In other variations, the PAA stream has less than 10,000 ppm, 1,000 ppm, 500 ppm, 100 ppm, 50 ppm, 10 ppm, or a range including any two of the aforementioned values, of radical polymerization inhibitors.

In some embodiments, the PAA is substantially free of anti-foam agents. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of anti-foam agents. In other variations, the PAA stream has less than 10,000 ppm, 1,000 ppm, 500 ppm, 100 ppm, 50 ppm, 10 ppm, or a range including any two of the aforementioned values, of anti-foam agents.

In certain embodiments, the inlet to the fourth reactor (also referred to as the PAA reactor) is further fed by one or more reactant streams each comprising a monomer to co-polymerize with GAA to form one or more co-polymers of PAA selected from a polyacrylamide copolymer, ethylene maleic anhydride copolymer, cross-linked carboxymethyl-cellulose copolymer, polyvinyl alcohol copolymer, cross-linked polyethylene oxide copolymer, and starch grafted polyacrylonitrile copolymer of PAA.

In certain embodiments, the system further comprises:
(v) a fifth reactor, comprising an inlet fed by the outlet stream comprising PAA, or a salt thereof, of the fourth reactor, a fifth reaction zone that converts at least some of the PAA, or a salt thereof, to superabsorbent polymer (SAP) and an outlet which provides an outlet stream comprising the SAP.

In one variation, the systems described herein further comprise:

a SAP reactor, comprising:
an inlet configured to receive PAA from the PAA stream,
a reaction zone configured to convert at least some of the PAA, or a salt thereof, to SAP, and
an outlet configured to provide a SAP stream comprising the SAP.

In certain embodiments, the inlet to the fifth reactor (also referred to as the SAP reactor) is further fed by one or more reactant streams each comprising a cross-linking agent may be sprayed on the PAA, or a salt thereof.

It should generally be understood that reference to "a first reaction zone" and "a second reaction zone", etc., or "a first reactor" and "a second reactor", etc., or "a first stream" and "a second stream", etc., does not necessarily imply an order of the reaction zones, reactors or streams. In some variations, the use of such references denotes the number of reaction zones, reactors or streams present. In other variations, an order may be implied by the context in which the reaction zones, reactors or streams are configured or used.

In certain embodiments, the SAP comprises less than about 1000 parts per million residual monoethylenically unsaturated monomer. In certain embodiments, the SAP is substantially free of an aldehyde impurity or a compound that derives from the oxidation of propylene.

In some embodiments, the SAP is substantially free of an aldehyde impurity. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of an aldehyde impurity. In other variations, the SAP stream has less than 10,000 ppm, 1,000 ppm, 500 ppm, 100 ppm, 50 ppm, 10 ppm, or a range including any two of the aforementioned values, of an aldehyde impurity.

In other variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of a compound that derives from the oxidation of propylene. In other variations, the SAP stream has less than 10,000 ppm, 1,000 ppm, 500 ppm, 100 ppm, 50 ppm, 10 ppm, or a range including any two of the aforementioned values, of a compound that derives from the oxidation of propylene.

In some embodiments, the SAP is substantially free of furfural. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of furfural. In other variations, the SAP stream has less than 10,000 ppm, 1,000 ppm, 500 ppm, 100 ppm, 50 ppm, 10 ppm, or a range including any two of the aforementioned values, of furfural.

In some embodiments, the SAP is substantially free of acetic acid. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of acetic acid. In other variations, the SAP stream has less than 10,000 ppm, 1,000 ppm, 500 ppm, 100 ppm, 50 ppm, 10 ppm, or a range including any two of the aforementioned values, of acetic acid.

In some embodiments, the SAP is substantially free of stabilizers. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of stabilizers. In other variations, the SAP stream has less than 10,000 ppm, 1,000 ppm, 500 ppm, 100 ppm, 50 ppm, 10 ppm, or a range including any two of the aforementioned values, of stabilizers.

In some embodiments, the SAP is substantially free of radical polymerization inhibitors. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of radical polymerization inhibitors. In other variations, the SAP stream has less than 10,000 ppm, 1,000 ppm, 500 ppm, 100 ppm, 50 ppm, 10 ppm, or a range including any two of the aforementioned values, of radical polymerization inhibitors.

In some embodiments, the SAP is substantially free of anti-foam agents. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of anti-foam agents. In other variations, the SAP stream has less than 10,000 ppm, 1,000 ppm, 500 ppm, 100 ppm, 50 ppm, 10 ppm, or a range including any two of the aforementioned values, of anti-foam agents.

In another aspect, an article is provided comprising any of the SAP provided herein.

In certain embodiments, the article is a disposable diaper, training pants, adult incontinence undergarment, or sanitary napkins. In certain embodiments, the article is a disposable diaper.

Methods

With reference to FIG. 1, an exemplary process to produce PAA and SAP from ethylene is depicted. The process depicted involves ethylene oxidation in step 100, carbonylation in step 200 to produce BPL and/or PPL, production of GAA in step 300, and production of PAA-SAP in step 400. In step 100, ethylene is fed into an oxidative reactor to produce ethylene oxide by an ethylene oxidation reaction. EO stream 110 comprising EO exits the oxidative reaction zone of the oxidative reactor. In step 200, EO stream 110 is fed into a central reactor for the conversion of EO and CO to BPL. In some variations, the entire EO stream 110 is fed into a central reactor. In other variations, a partial EO stream 110 is fed into a central reactor, e.g., to control the rate of EO entering the oxidative reactor. In step 200, EO stream 110 comprising EO, from the oxidative reaction zone, enters the central reactor as an inlet stream where it is combined with CO. Outlet streams comprising either BPL (stream 210) or PPL (stream 220) exit the central reactor.

In step 300, three alternatives are depicted to convert BPL and/or PPL to GAA using first, second (a), second (b) and third reactors. In one variation, in step 300, BPL stream 210 is directly converted to GAA in a first reactor. As depicted in FIG. 1, the central reactor may have an outlet configured to output BPL stream 210 (top stream depicted in FIG. 1) comprising BPL, and BPL stream 210 enters the first reactor as an inlet stream where it is converted to GAA.

In another variation, in step 300, BPL stream 210 is converted to GAA in a two-reactor system. As depicted in FIG. 1, the central reactor may have an outlet configured to output BPL (middle stream depicted in FIG. 1) stream 210 comprising BPL, and BPL stream 210 enters the second (a) reactor as an inlet stream where it is converted to PPL. In second (a) reactor, BPL stream 210 is polymerized to produce PPL, and in second (b) reactor, the PPL is pyrolyzed to produce GAA. An outlet stream comprising PPL, from the second (a) reactor, enters the second (b) reactor as an inlet stream where it is converted to GAA. In yet another variation, in step 300, PPL stream 220 is pyrolyzed to produce GAA. As depicted in FIG. 1, the central reactor may have an outlet configured to output PPL (bottom stream depicted in FIG. 1). PPL stream 220 comprising PPL, from the central reactor, enters the third reactor as an inlet stream where it is converted to GAA. First, second and third outlet streams comprising first, second and third GAA streams (collectively referred to as GAA stream 310) exit the first, second (b) and third reactors. In step 400, GAA is converted to PAA and/or SAP in first, second and third reactors.

It should generally be understood that, in other variations of the process described in FIG. 1, one or more steps may be added or omitted. For example, in some variations, EO stream 110 from the oxidative reactor is further treated (e.g., dried and/or purified) before feeding into the central reactor for the conversion of EO and CO to BPL in step 200. In other variation, step 100 may be omitted, and ethylene oxide obtained from any commercially available source may be fed into the central reactor in step 200.

In another aspect, a method is provided for the conversion of ethylene to polyacrylic acid (PAA), within an integrated system, the method comprising:

providing an inlet stream comprising ethylene to an oxidative reactor of the integrated system to effect conversion of at least a portion of the provided ethylene to EO, providing an inlet stream comprising EO from the oxidative reactor, and carbon monoxide (CO) to a central reactor of the integrated system, contacting the inlet stream with a metal carbonyl in a central reaction zone to effect conversion of at least a portion of the provided EO to a beta propiolactone (BPL), directing an outlet stream comprising BPL from the central reaction zone to at least one of:
  (i) a first reactor, comprising an inlet fed by the outlet stream comprising BPL of the central reactor, a first reaction zone that converts at least some of the BPL to AA, and an outlet from which an outlet stream comprising the AA is obtainable,
  (ii) a second (a) reactor, comprising an inlet fed by the outlet stream comprising BPL of the central reactor, a second (a) reaction zone that converts at least some of the BPL to PPL, and an outlet from which an outlet stream comprising the PPL is obtainable, and a second (b) reactor, comprising an inlet fed by the outlet stream comprising PPL of the second (a) reactor, a second (b) reaction zone that converts at least some of the PPL to AA, and an outlet from which an outlet stream comprising the AA is obtainable,
  (iii) a third reactor, comprising an inlet fed by the outlet stream comprising PPL of the central reactor, a third reaction zone that converts at least some of the PPL to a third product, and an outlet from which an outlet stream comprising the AA is obtainable, and obtaining AA; and providing an outlet stream comprising AA from one or more of the first, second (b) and third reactor, to the inlet of: (iv) a fourth reactor in which at least some of the AA is converted to polyacrylic acid (PAA), or a salt thereof.

In some variations, the AA is glacial AA (GAA).

In some embodiments, provided is a method for converting ethylene to polyacrylic acid (PAA), within an integrated system, the method comprising:

providing an inlet stream comprising ethylene to an oxidative reactor of the integrated system to effect conversion of at least a portion of the provided ethylene to EO, providing an inlet stream comprising EO from the oxidative reactor, and carbon monoxide (CO) to a central reactor of the integrated system, contacting the inlet stream with a metal carbonyl in a central reaction zone to effect conversion of at least a portion of the provided EO to a beta propiolactone (BPL) stream comprising BPL and/or a polypropiolactone (PPL) outlet stream comprising PPL, directing an outlet stream from the central reaction zone to at least one of (i)-(iii):
  (i) a first reactor, comprising an inlet fed by BPL from the outlet stream of the central reactor, a first reaction zone that converts at least some of the BPL to AA, and an outlet from which an outlet stream comprising the AA is obtainable,
  (ii) a second (a) reactor, comprising an inlet fed with BPL from the outlet stream of the central reactor, a second (a) reaction zone that converts at least some of the BPL to PPL, and an outlet from which an outlet stream comprising the PPL is obtainable, and a second (b) reactor, comprising an inlet fed by the outlet stream comprising PPL of the second (a) reactor, a second (b) reaction zone that converts at least some of the PPL to AA, and an outlet from which an outlet stream comprising the AA is obtainable,
  (iii) a third reactor, comprising an inlet fed by PPL from the PPL outlet stream of the central reactor, a third reaction zone that converts at least some of the PPL to AA, and an outlet from which an outlet stream comprising the AA is obtainable, and obtaining AA; and providing an outlet stream comprising AA from one or more of the first, second (b) and third reactor, to the inlet of: (iv) a fourth reactor in which at least some of the AA is converted to polyacrylic acid (PAA), or a salt thereof.

In one variation, the AA is glacial AA (GAA).

In some variations, provided is a method for converting ethylene to polyacrylic acid (PAA), within an integrated system, the method comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to beta propiolactone (BPL) or polypropiolactone (PPL), or a combination thereof, in the central reaction zone to produce a carbonylation stream comprising BPL, or a carbonylation stream comprising PPL, or a combination thereof;

(i) directing the carbonylation stream comprising BPL to an AA reactor (also referred to in FIG. 1 as first reactor), and converting at least some of the BPL in the carbonylation stream to AA in the AA reactor to produce an AA stream comprising the AA; or (ii) directing the carbonylation stream comprising BPL to a PPL reactor (also referred to in FIG. 1 as second (a) reactor), converting at least some of the BPL in the carbonylation stream to PPL in the PPL reactor to produce a PPL stream comprising PPL, directing the PPL stream to an AA reactor (also referred to in FIG. 1 as second (b) reactor), and converting at least some of the PPL to AA in the AA reactor to produce an AA stream; or (iii) directing the carbonylation stream comprising PPL to an AA reactor (also referred to in FIG. 1 as third reactor), and converting at least some of the PPL in the carbonylation stream to AA in the AA reactor to produce an AA stream comprising AA; or any combinations of (i)-(iii) above;

directing the AA streams of (i)-(iii) above to a PAA reactor; and converting at least a portion of the AA of the AA streams of (i)-(iii) above to polyacrylic acid (PAA), or a salt thereof, in the PAA reactor.

In certain variations, the method comprises (i). Thus, in some variations, provided is a method for converting ethylene to polyacrylic acid (PAA), within an integrated system, comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to beta propiolactone (BPL) in the central reaction zone to produce a carbonylation stream comprising BPL;

directing the carbonylation stream to an AA reactor (also referred to in FIG. 1 as first reactor);

converting at least some of the BPL of the carbonylation stream to AA in the AA reactor to produce an AA stream comprising the AA;

directing AA from the AA stream to a PAA reactor (also referred to in FIG. 1 as fourth reactor); and converting at least a portion of the AA of the AA stream to polyacrylic acid (PAA), or a salt thereof, in the PAA reactor.

In other variations, the method comprises (ii). Thus, in other variations, provided is a method for converting ethylene to polyacrylic acid (PAA), within an integrated system, the method comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to beta propiolactone (BPL) in the central reaction zone to produce a carbonylation stream comprising BPL;

directing the carbonylation stream to a PPL reactor (also referred to in FIG. 1 as second (a) reactor);

converting at least some of the BPL in the carbonylation stream to PPL in the PPL reactor to produce a PPL stream comprising the PPL;

directing PPL from the PPL stream to an AA reactor (also referred to in FIG. 1 as second (b) reactor);

converting at least some of the PPL in the PPL stream to AA in the AA reactor to produce an AA stream comprising the AA;

directing AA from the AA stream to a PAA reactor (also referred to in FIG. 1 as fourth reactor); and converting at least a portion of the AA of the AA stream to polyacrylic acid (PAA), or a salt thereof, in the PAA reactor.

In yet other variations, the method comprises (iii). Thus, in yet other variations, provided is a method for converting ethylene to polyacrylic acid (PAA), within an integrated system, the method comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to polypropiolactone (PPL) in the central reaction zone to produce a carbonylation stream comprising PPL;

directing PPL from the carbonylation stream to an AA reactor (also referred to in FIG. 1 as third reactor);

converting at least some of the PPL in the carbonylation stream to AA in the AA reactor to produce an AA stream comprising the AA;

directing AA from the AA stream to a PAA reactor (also referred to in FIG. 1 as fourth reactor); and converting at least a portion of the AA the AA stream to polyacrylic acid (PAA), or a salt thereof, in the PAA reactor.

In one embodiment, the method comprises (i) and (iii). Thus, in one variation, provided is a method for converting ethylene to polyacrylic acid (PAA), within an integrated system, the method comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to beta propiolactone (BPL) and polypropiolactone (PPL) in the central reaction zone to produce a first carbonylation stream comprising BPL and a second carbonylation stream comprising PPL;

directing BPL from the first carbonylation stream to a first AA reactor (also referred to in FIG. 1 as first reactor);

converting at least some of the BPL of the first carbonylation stream to AA in the first AA reactor to produce a first AA stream comprising the AA;

directing PPL from the second carbonylation stream to a second AA reactor (also referred to in FIG. 1 as third reactor);

converting at least some of the PPL of the second carbonylation stream to AA in the second AA reactor to produce a second AA stream comprising the AA;

directing AA from the first AA stream, the second AA stream, or a combination thereof, to a PAA reactor; and converting at least a portion of the AA of the first AA stream, the second AA stream, or a combination thereof, to polyacrylic acid (PAA), or a salt thereof, in the PAA reactor.

In some variations of the foregoing method, the first and second AA reactors are the same reactor. In other variations, the first and second AA reactors are separate reactors.

In some variations of the foregoing method where the first and second AA reactors are separate reactors, the PAA reactor is fed with AA from both of the AA streams. For example, AA from the first AA stream and AA from the second AA stream may be combined at the PAA reactor, and in some variations, this combination may occur either at the inlet of the PAA reactor or at a point prior to the PAA reactor inlet. In other variations, the PAA is fed with AA exclusively from the first AA stream or exclusively from the second AA stream. In some variations the method includes controlling the ratio of the AA provided from the first AA stream and AA provided from the second AA stream or changing the ratio of the AA source fed to the PAA reactor over time.

In one embodiment, the method comprises (ii) and (iii). Thus, in one variation, provided is a method for converting ethylene to polyacrylic acid (PAA), within an integrated system, the method comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to beta propiolactone (BPL) and polypropiolactone (PPL) in the central reaction zone to produce a first carbonylation stream comprising BPL, and a second carbonylation stream comprising PPL;

directing BPL from the first carbonylation stream to a PPL reactor (also referred to in FIG. 1 as second (a) reactor);

converting at least some of the BPL of the first carbonylation stream to PPL in the PPL reactor to produce a PPL stream comprising the PPL;

directing PPL from the PPL stream to a first AA reactor (also referred to in FIG. 1 as second (b) reactor);

converting at least some of the PPL of the PPL stream to AA in the first AA reactor to produce a first AA stream comprising the AA;

directing PPL from the second carbonylation stream to a second AA reactor (also referred to in FIG. 1 as third reactor);

converting at least some of the PPL of the second carbonylation stream to AA in the second AA reactor to produce a second AA stream comprising the AA;

directing AA from the first AA stream, the second AA stream, or a combination thereof, to a PAA reactor; and converting at least a portion of the AA of the first AA stream, the second AA stream, or a combination thereof, to polyacrylic acid (PAA), or a salt thereof, in the PAA reactor.

In some variations of the foregoing method, the first and second AA reactors are the same reactor. In other variations, the first and second AA reactors are separate reactors.

In some variations of the foregoing method, the PAA reactor is configured to receive AA from both of the AA streams. For example, the PAA reactor may be fed with AA from the first AA stream and AA from the second AA stream, and in some variations, the combination of AA from the two AA streams may occur either at the inlet of the PAA reactor or at a point prior to the PAA reactor inlet. In other variations, the PAA reactor is fed with AA exclusively from the first AA stream or exclusively with AA from the second AA stream. In some variations the method includes controlling the source of the AA provided to the PAA reactor and/or to controlling the ratio of AA supplied from the first AA stream and the second AA stream. In some variations, the method includes changing the AA source or the ratio AA from the two sources over time.

In another embodiment, the method comprises (i) and (ii). Thus, in one variation, provided is a method for converting ethylene to polyacrylic acid (PAA), within an integrated system, the method comprising:

providing an ethylene stream comprising ethylene to an oxidative reactor of the integrated system;

converting at least a portion of the ethylene in the ethylene stream to ethylene oxide (EO) in the oxidative reactor to produce an EO stream comprising the EO;

providing the EO stream from the oxidative reactor, and a carbon monoxide (CO) stream comprising CO to a central reaction zone of the integrated system;

contacting the EO stream and the CO stream with a metal carbonyl in the central reaction zone;

converting at least a portion of the EO in the EO stream to beta propiolactone (BPL) in the central reaction zone to produce a carbonylation stream comprising BPL;

directing at least a portion of the carbonylation stream to a first AA reactor (also referred to in FIG. 1 as first reactor);

converting at least some of the BPL of the carbonylation stream to AA in the first AA reactor to produce a first AA stream comprising the AA;

directing at least a portion of the carbonylation stream to a PPL reactor (also referred to in FIG. 1 as second (a) reactor);

converting at least some of the BPL of the carbonylation stream to PPL in the PPL reactor to produce a PPL stream comprising the PPL;

directing PPL from the PPL stream to a second AA reactor (also referred to in FIG. 1 as second (b) reactor);

converting at least some of the PPL of the PPL stream to AA in the second AA reactor to produce a second AA stream comprising the AA;

directing AA from the first AA stream, AA from the second AA stream, or a combination thereof, to a PAA reactor; and converting at least a portion of the AA of the first AA stream, the second AA stream, or a combination thereof, to polyacrylic acid (PAA), or a salt thereof, in the PAA reactor.

In some variations of the foregoing method, the first and second AA reactors are the same reactor. In other variations, the first and second AA reactors are separate reactors.

In some variations of the foregoing method, the PAA reactor is configured to receive AA from both of the AA streams. For example, the PAA reactor may be fed with AA from the first AA stream and AA from the second AA stream, and in some variations, the combination of AA from the two AA streams may occur either at the inlet of the PAA reactor or at a point prior to the PAA reactor inlet. In other variations, the PAA reactor is fed with AA exclusively from the first AA stream or exclusively with AA from the second AA stream. In some variations, the method includes controlling the source of the AA provided to the PAA reactor and/or to controlling the ratio of AA supplied from the first AA stream and the second AA stream. In some variations, the method includes changing the AA source or the ratio AA from the two sources over time.

In certain embodiments of the foregoing methods, the AA stream is substantially free of an aldehyde impurity or a compound that derives from the oxidation of propylene. In some embodiments, the AA is substantially free of an aldehyde impurity. In some variations of the methods, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of an aldehyde impurity. In other variations, the AA stream has less than 10,000 ppm, 1,000 ppm, 500 ppm, 100 ppm, 50 ppm, 10 ppm, or a range including any two of the aforementioned values, of an aldehyde impurity.

In other variations of the methods, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of a compound that derives from the oxidation of propylene. In other variations, the AA stream has less than 10,000 ppm, 1,000 ppm, 500 ppm, 100 ppm, 50 ppm, 10 ppm, or a range including any two of the aforementioned values, of a compound that derives from the oxidation of propylene.

In some embodiments, the AA is substantially free of furfural. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of furfural. In other variations, the AA stream has less than 10,000 ppm, 1,000 ppm, 500 ppm, 100 ppm, 50 ppm, 10 ppm, or a range including any two of the aforementioned values, of furfural.

In some embodiments, the AA is substantially free of acetic acid. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of acetic acid. In other variations, the AA stream has less than 10,000 ppm, 1,000 ppm, 500 ppm, 100 ppm, 50 ppm, 10 ppm, or a range including any two of the aforementioned values, of acetic acid.

In some embodiments, the AA is substantially free of stabilizers. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of stabilizers. In other variations, the AA stream has less than 10,000 ppm, 1,000 ppm, 500 ppm, 100 ppm, 50 ppm, 10 ppm, or a range including any two of the aforementioned values, of stabilizers.

In some embodiments, the AA is substantially free of radical polymerization inhibitors. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of radical polymerization inhibitors. In other variations, the AA stream has less than 10,000 ppm, 1,000 ppm, 500 ppm, 100 ppm, 50 ppm, 10 ppm, or a range including any two of the aforementioned values, of radical polymerization inhibitors.

In some embodiments, the AA is substantially free of anti-foam agents. In some variations, the AA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of anti-foam agents. In other variations, the AA stream has less than 10,000 ppm, 1,000 ppm, 500 ppm, 100 ppm, 50 ppm, 10 ppm, or a range including any two of the aforementioned values, of anti-foam agents.

In certain embodiments of the foregoing methods, the AA directed from the AA streams is glacial acrylic acid (GAA). In some variations, AA has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

In certain embodiments of the foregoing methods, the GAA is substantially free of an aldehyde impurity or a compound that derives from the oxidation of propylene. In some embodiments, the GAA is substantially free of an aldehyde impurity. In some variations of the foregoing methods, the GAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of an aldehyde impurity. In other variations, the GAA stream has less than 10,000 ppm, 1,000 ppm, 500 ppm, 100 ppm, 50 ppm, 10 ppm, or a range including any two of the aforementioned values, of an aldehyde impurity.

In other variations of the methods, the GAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of a compound that derives from the oxidation of propylene. In other variations, the GAA stream has less than 10,000 ppm, 1,000 ppm, 500 ppm, 100 ppm, 50 ppm, 10 ppm, or a range including any two of the aforementioned values, of a compound that derives from the oxidation of propylene.

In some embodiments, the GAA is substantially free of furfural. In some variations, the GAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of furfural. In other variations, the GAA stream has less than 10,000 ppm, 1,000 ppm, 500 ppm, 100 ppm, 50 ppm, 10 ppm, or a range including any two of the aforementioned values, of furfural.

In some embodiments, the GAA is substantially free of acetic acid. In some variations, the GAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of acetic acid. In other variations, the GAA stream has less than 10,000 ppm, 1,000 ppm, 500 ppm, 100 ppm, 50 ppm, 10 ppm, or a range including any two of the aforementioned values, of acetic acid.

In some embodiments, the GAA is substantially free of stabilizers. In some variations, the GAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of stabilizers. In other variations, the GAA stream has less than 10,000 ppm, 1,000 ppm, 500 ppm, 100 ppm, 50 ppm, 10 ppm, or a range including any two of the aforementioned values, of stabilizers.

In some embodiments, the GAA is substantially free of radical polymerization inhibitors. In some variations, the GAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of radical polymerization inhibitors. In other variations, the GAA stream has less than 10,000 ppm, 1,000 ppm, 500 ppm, 100 ppm, 50 ppm, 10 ppm, or a range including any two of the aforementioned values, of radical polymerization inhibitors.

In some embodiments, the GAA is substantially free of anti-foam agents. In some variations, the GAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of anti-foam agents. In other variations, the GAA stream has less than 10,000 ppm, 1,000 ppm, 500 ppm, 100 ppm, 50 ppm, 10 ppm, or a range including any two of the aforementioned values, of anti-foam agents.

In certain embodiments of the foregoing methods, the PAA, or a salt thereof, is substantially free of an aldehyde impurity or a compound that derives from the oxidation of propylene. In some embodiments, the PAA is substantially free of an aldehyde impurity. In some embodiments, the PAA stream is substantially free of an aldehyde impurity. In some variations, the AA outlet stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of an aldehyde impurity. In other variations, the PAA stream has less than 10,000 ppm, 1,000 ppm, 500 ppm, 100 ppm, 50 ppm, 10 ppm, or a range including any two of the aforementioned values, of an aldehyde impurity.

In other variations of the methods, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of a compound that derives from the oxidation of propylene. In other variations, the PAA stream has less than 10,000 ppm, 1,000 ppm, 500 ppm, 100 ppm, 50 ppm, 10 ppm, or a range including any two of the aforementioned values, of a compound that derives from the oxidation of propylene.

In some embodiments, the PAA is substantially free of furfural. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of furfural. In other variations, the PAA stream has less than 10,000 ppm, 1,000 ppm, 500 ppm, 100 ppm, 50 ppm, 10 ppm, or a range including any two of the aforementioned values, of furfural.

In some embodiments, the PAA is substantially free of acetic acid. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of acetic acid. In other variations, the PAA stream has less than 10,000 ppm, 1,000 ppm, 500 ppm, 100 ppm, 50 ppm, 10 ppm, or a range including any two of the aforementioned values, of acetic acid.

In some embodiments, the PAA is substantially free of stabilizers. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of stabilizers. In other variations, the PAA stream has less than 10,000 ppm, 1,000 ppm, 500 ppm, 100 ppm, 50 ppm, 10 ppm, or a range including any two of the aforementioned values, of stabilizers.

In some embodiments, the PAA is substantially free of radical polymerization inhibitors. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of radical polymerization inhibitors. In other variations, the PAA stream has less than 10,000 ppm, 1,000 ppm, 500 ppm, 100 ppm, 50 ppm, 10 ppm, or a range including any two of the aforementioned values, of radical polymerization inhibitors.

In some embodiments, the PAA is substantially free of anti-foam agents. In some variations, the PAA stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of anti-foam agents. In other variations, the PAA stream has less than 10,000 ppm, 1,000 ppm, 500 ppm, 100 ppm, 50 ppm, 10 ppm, or a range including any two of the aforementioned values, of anti-foam agents.

In certain embodiments, the PAA, or a salt thereof, is formulated for use in compositions for paper treatment, water treatment, or detergent co-builder applications.

In certain embodiments, the method further comprises:
providing PAA from an outlet stream comprising PAA, or a salt thereof, from the fourth reactor, to the inlet of: (v) a fifth reactor in which at least some of the PAA, or a salt thereof, is converted to superabsorbent polymer (SAP).

In some variations, the method further comprises:
providing a PAA stream comprising PAA, or a salt thereof, from the PAA reactor;
directing PAA from the PAA stream to a superabsorbent polymer (SAP) reactor; and
converting at least a portion of the PAA in the PAA stream to SAP in the SAP reactor.

In certain embodiments of the foregoing method, the SAP comprises less than about 1000 parts per million residual monoethylenically unsaturated monomer. In certain embodiments, the SAP is substantially free of an aldehyde impurity or a compound that derives from the oxidation of propylene. In some embodiments, the SAP is substantially free of an aldehyde impurity. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of an aldehyde impurity. In other variations, the SAP stream has less than 10,000 ppm, 1,000 ppm, 500 ppm, 100 ppm, 50 ppm, 10 ppm, or a range including any two of the aforementioned values, of an aldehyde impurity.

In other variations of the methods, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of a compound that derives from the oxidation of propylene. In other variations, the SAP stream has less than 10,000 ppm, 1,000 ppm, 500 ppm, 100 ppm, 50 ppm, 10 ppm, or a range including any two of the aforementioned values, of a compound that derives from the oxidation of propylene.

In some embodiments, the SAP is substantially free of furfural. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of furfural. In other variations, the SAP stream has less than 10,000 ppm, 1,000 ppm, 500 ppm, 100 ppm, 50 ppm, 10 ppm, or a range including any two of the aforementioned values, of furfural.

In some embodiments, the SAP is substantially free of acetic acid. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of acetic acid. In other variations, the SAP stream has less than 10,000 ppm, 1,000 ppm, 500 ppm, 100 ppm, 50 ppm, 10 ppm, or a range including any two of the aforementioned values, of acetic acid.

In some embodiments, the SAP is substantially free of stabilizers. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of stabilizers. In other variations, the SAP stream has less than 10,000 ppm, 1,000 ppm, 500 ppm, 100 ppm, 50 ppm, 10 ppm, or a range including any two of the aforementioned values, of stabilizers.

In some embodiments, the SAP is substantially free of radical polymerization inhibitors. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of radical polymerization inhibitors. In other variations, the SAP stream has less than 10,000 ppm, 1,000 ppm, 500 ppm, 100 ppm, 50 ppm, 10 ppm, or a range including any two of the aforementioned values, of radical polymerization inhibitors.

In some embodiments, the SAP is substantially free of anti-foam agents. In some variations, the SAP stream has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of anti-foam agents. In other variations, the SAP stream has less than 10,000 ppm, 1,000 ppm, 500 ppm, 100 ppm, 50 ppm, 10 ppm, or a range including any two of the aforementioned values, of anti-foam agents.

In some embodiments of the foregoing method, the GAA is converted to PAA less than two weeks after the ethylene is converted to EO. In some embodiments, GAA is converted to PAA less than one week after the ethylene is converted to EO. In some embodiments, GAA is converted to PAA less than six, five, four, three, two days after the ethylene is converted to EO. In some embodiments, GAA is converted to PAA less than 24 hours after the ethylene is converted to EO.

The sections below more fully describe elements of the integrated system and methods as well as some of the reactions and conditions for effecting the conversion of ethylene to PAA and to SAP.

Controller

The controller can be any integrated means (e.g., a computer-based network) to monitor, control and/or modulate (e.g., increase, decrease or maintain) all processes and components related to the disclosed system, including all reaction zones (via sensors, switches, valves, vacuum, pumps etc.). The controller can independently modulate production of the BPL by the central reactor, production of the EO in an oxidative reactor, if present, and production for each of the BPL, PPL, AA, PAA, and SAP products, in their respective reactors, by, e.g., independently controlling temperatures and pressures in each reaction zone and flow rates for inlet and outlet streams.

In some embodiments, the controller is used to independently increase, decrease or maintain production of the EO, BPL, PPL, AA, PAA, or a salt thereof, and SAP by respective reactors within the integrated system.

Ethylene to EO

The disclosed system optionally further includes, at its upstream end, an oxidative reactor that produces EO on-site and provides EO to the central reactor. In certain embodiments, EO is obtained directly from the gas phase oxidation of ethylene. This embodiment is advantageous in that it avoids the need to isolate, store, and transport ethylene oxide which is both toxic and explosive. In certain embodiments, the ethylene oxide is maintained in the gas phase as produced and fed to the central reactor without condensing it to a liquid.

Another benefit of producing EO on-site includes a considerable increase in the plant's capacity to produce greater quantities of $C_3$ and/or $C_4$ products. In certain embodiments, the system can produce any combination of $C_3$ and/or $C_4$ products at a rate of about 200, 250, 300, 350, 400, 450, 500, 550, 600, 650, 700, 750, 800, 850, 900, 950, 1,000 kilotons per annum (kta), or within a range including any two of these values.

Thus, in certain embodiments, the system further comprises an oxidative reactor, comprising an inlet fed by ethylene, an oxidative reaction zone that converts at least some of the ethylene to EO, and an outlet which provides an outlet stream comprising the EO, which is fed to the inlet of the central reactor.

Alternatively, in other embodiments, EO is not produced within the disclosed system. Rather, in such embodiments, an upstream oxidative reactor is absent and the central reactor is fed EO that was produced off-site.

EO to BPL

In certain embodiments, the disclosed system includes a central reactor for carbonylation of EO into BPL via a "carbonylation reaction." The central reactor receives the EO (e.g., from the EO source) and CO (e.g., from the CO source), as well as the carbonylation catalyst and solvents, etc. and carries out the carbonylation reaction of the EO in the central reaction zone. In certain embodiments, the EO and CO are received at separate inputs. In certain embodiments, the EO and CO are received as a mixture. In certain embodiments, the EO/CO mixture received is gaseous. In certain embodiments, the carbonylation reaction is continuous. Such continuous carbonylation reactions can be conducted in a continuous stirred tank reactor or a plug flow reactor such that BPL solution is withdrawn at essentially the same rate it is formed.

In certain embodiments, the carbonylation reaction of EO to BPL proceeds as shown below:

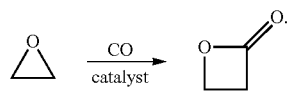

Carbonylation Reaction Conditions

Methods of making BPL are known in the art and include those described in WO2013/063191 and WO2014/004858. Suitable catalysts and reaction conditions for effecting the above reactions are described herein and also disclosed in published PCT applications: WO2003/050154, WO2004/089923, WO2012/158573, WO2010/118128, WO2013/063191, and WO2014/008232; in U.S. Pat. Nos. 5,359,081 and 5,310,948 and in the publication "Synthesis of beta-Lactones" *J. Am. Chem. Soc.*, vol. 124, 2002, pages 1174-1175.

In certain embodiments, the central reactor, comprising an inlet, is fed by a "reaction stream" comprising EO and CO. In certain embodiments, the reaction stream fed into the carbonylation reaction comprises a gaseous mixture containing EO and CO. In certain embodiments, the molar ratio of CO to EO in the reaction stream ranges from about 1:1 to about 10,000:1. In certain embodiments, the molar ratio of CO to EO in the reaction stream is about 5000:1, is about 2500:1, is about 2000:1, is about 1500:1, is about 1000:1, is about 500:1, is about 1:500, is about 200:1, is about 100:1, is about 50:1, is about 20:1, is about 10:1, is about 5:1 or is about 1:1, or within a range including any two of these ratios.

In certain embodiments, the reaction stream further comprises one or more additional components. In certain embodiments, the additional components comprise diluents which do not directly participate in the chemical reactions of EO. In certain embodiments, such diluents may include one or more inert gases (e.g., nitrogen, argon, helium and the like) or volatile organic molecules such as hydrocarbons, ethers, and the like. In certain embodiments, the reaction stream may comprise hydrogen, traces of carbon dioxide, methane, and other compounds commonly found in industrial CO streams. In certain embodiments, the feed stream may further comprise materials that may have a direct or indirect chemical function in one or more of the processes involved in the conversion of EO to BPL and various end products. Additional reactants can also include mixtures of CO and another gas. For example, as noted above, In certain embodiments, CO is provided in a mixture with hydrogen (e.g., Syngas).

In certain embodiments, the reaction stream is characterized in that it is essentially free of oxygen. In certain embodiments, the reaction stream is characterized in that it is essentially free of water. In certain embodiments, the reaction stream is characterized in that it is essentially free of oxygen and water.

Carbonylation Solvents

In certain embodiments, the carbonylation reaction described herein is performed in a solvent. In certain embodiments, the solvent is fed to the central reaction zone as a separate stream. In other embodiments, the solvent may be fed to the central reaction zone along with the catalyst, EO or another feed stream entering the carbonylation reaction in the central reaction zone. In certain embodiments, the solvent enters the central reaction zone along with the carbonylation catalyst which is provided as a catalyst solution in the solvent. In certain embodiments, the solvent enters the central reaction zone in two or more separate feed streams. In embodiments where solvent is present in the central reaction zone, it may also be present in the carbonylation outlet stream.

The solvent may be selected from any solvent, and mixtures of solvents. Additionally, BPL may be utilized as a co-solvent. Solvents most suitable for the methods include ethers, hydrocarbons and non protic polar solvents. Suitable solvents include, for example, tetrahydrofuran ("THF"), sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, dimethoxy ethane, acetone, and methylethyl ketone.

In certain embodiments, the carbonylation reaction further includes a Lewis base additive to the carbonylation reaction in the central reaction zone. In some embodiments such Lewis base additives can stabilize or reduce deactivation of the catalysts. In certain embodiments, the Lewis base additive is selected from the group consisting of phosphines, amines, guanidines, amidines, and nitrogen-containing heterocycles. In certain embodiments, the Lewis base additive is a phosphine. In certain embodiments, the Lewis base additive is a hindered amine base. In certain embodiments, the Lewis base additive is a 2,6-lutidine; imidazole, 1-methylimidazole, 4-dimethylaminopyridine, trihexylamine and triphenylphosphine.

Carbonylation Catalysts

Numerous carbonylation catalysts known in the art are suitable for (or can be adapted to) methods described herein. For example, in some embodiments, the carbonylation methods utilize a metal carbonyl-Lewis acid catalyst such as those described in U.S. Pat. No. 6,852,865. In other embodiments, the carbonylation is performed with one or more of the carbonylation catalysts disclosed in U.S. patent application Ser. No. 10/820,958; and Ser. No. 10/586,826. In other embodiments, the carbonylation is performed with one or more of the catalysts disclosed in U.S. Pat. Nos. 5,310,948; 7,420,064; and 5,359,081. Additional catalysts for the carbonylation of epoxides are discussed in a review in Chem. Commun., 2007, 657-674.

In some embodiments, the carbonylation catalyst includes a metal carbonyl compound. Typically, in one variation, a single metal carbonyl compound is provided, but in some embodiments, mixtures of two or more metal carbonyl compounds are provided. Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more metal carbonyl compounds. Preferably, the provided metal carbonyl compound is capable of ring-opening an epoxide and facilitating the insertion of CO into the resulting metal carbon bond. Metal carbonyl compounds with this reactivity are well known in the art and are used for laboratory experimentation as well as in industrial processes such as hydroformylation.

In some embodiments, the metal carbonyl compound comprises an anionic metal carbonyl moiety. In other embodiments, the metal carbonyl compound comprises a neutral metal carbonyl compound. In some embodiments, the metal carbonyl compound comprises a metal carbonyl hydride or a hydrido metal carbonyl compound. In some embodiments, the metal carbonyl compound acts as a precatalyst which reacts in situ with one or more reaction components to provide an active species different from the compound initially provided. Such pre-catalysts are specifically encompassed as it is recognized that the active species in a given reaction may not be known with certainty; thus the identification of such a reactive species in situ does not itself depart from the spirit or teachings herein.

In some embodiments, the metal carbonyl compound comprises an anionic metal carbonyl species. In some embodiments, such anionic metal carbonyl species have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In some embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, for example, $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$. In some embodiments, the anionic metal carbonyl comprises $[Co(CO)_4]^-$. In some embodiments, a mixture of two or more anionic metal carbonyl complexes may be present in the carbonylation catalysts used in the methods.

The term "such as to provide a stable anionic metal carbonyl" for $[Q_dM'_e(CO)_w]^{y-}$ is used herein to mean that $[Q_dM'_e(CO)_w]^{y-}$ is a species that may be characterized by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments where the provided metal carbonyl compound is an anionic species, one or more cations must also necessarily be present. No particular constraints are placed on the identity of such cations. In some embodiments, the cation associated with an anionic metal carbonyl compound comprises a reaction component of another category described herein below. For example, in some embodiments, the metal carbonyl anion is associated with a cationic Lewis acid. In other embodiments a cation associated with a provided anionic metal carbonyl compound is a simple metal cation such as those from Groups 1 or 2 of the periodic table (e.g., $Na^+$, $Li^+$, $K^+$, and $Mg^{2+}$). In other embodiments a cation associated with a provided anionic metal carbonyl compound is a bulky non electrophilic cation such as an 'onium salt' (e.g., $Bu_4N^+$, $PPN^+$, $Ph_4P^+$, and $Ph_4As^+$). In other embodiments, a metal carbonyl anion is associated with a protonated nitrogen compound (e.g., a cation may comprise a compound such as $MeTBD-H^+$, $DMAP-H^+$, $DABCO-H^+$, and $DBU-H^+$). In some embodiments, compounds comprising such protonated nitrogen compounds are provided as the reaction product between an acidic hydrido metal carbonyl compound and a basic nitrogen-containing compound (e.g., a mixture of DBU and $HCo(CO)_4$).

In some embodiments, a catalyst utilized in the methods described herein comprises a neutral metal carbonyl compound. In some embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula $QM'(CO)_{w'}$. In some embodiments, the neutral metal carbonyl has the general formula $M'(CO)_{w'}$. In some embodiments, the neutral metal carbonyl has the general formula $QM'_2(CO)_{w'}$. In some embodiments, the neutral metal carbonyl has the general formula $M'_2(CO)_{w'}$. Suitable neutral metal carbonyl compounds include, for example, $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$. The term "such as to provide a stable neutral metal carbonyl" for $Q_dM'_e(CO)_{w'}$ is used herein to mean that $Q_dM'_e(CO)_{w'}$ is a species that may be characterized by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine. In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In some embodiments, the carbonylation catalyst utilized in the methods described above further includes a Lewis acidic component. In some embodiments, the carbonylation catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In some embodiments, where an included Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., $R_2BX$), a dihalo monoalkyl compound (e.g., $RBX_2$), an aryl halo boron compound (e.g., $Ar_2BX$ or $ArBX_2$), or a trihalo boron compound (e.g., $BCl_3$ or $BBr_3$), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where carbonylation catalysts used in methods described herein include a cationic metal complex, the metal complex has the formula $[(L^c)_vM_b]^{z+}$, where:

$L^c$ is a ligand where, when two or more $L^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

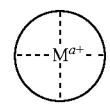

I wherein:

⊕ is a multidentate ligand;

M is a metal atom coordinated to the multidentate ligand; and a is the charge of the metal atom and ranges from 0 to 2.

In some embodiments, provided metal complexes conform to structure II:

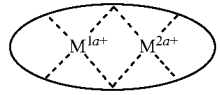
II wherein a is as defined above (each a may be the same or different), and M¹ is a first metal atom;

M² is a second metal atom; and

 comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, for example, porphyrin ligands 1, salen ligands 2, dibenzotetramethyltetraaza[14]annulene (tmtaa) ligands 3, phthalocyaninate ligands 4, the Trost ligand 5, tetraphenylporphyrin ligands 6, and corrole ligands 7. In some embodiments, the multidentate ligand is a salen ligands. In other embodiments, the multidentate ligand is a porphyrin ligands. In other embodiments, the multidentate ligand is a tetraphenylporphyrin ligands. In other embodiments, the multidentate ligand is a corrole ligands. Any of the foregoing ligands can be unsubstituted or can be substituted. Numerous variously substituted analogs of these ligands are known in the art and will be apparent to the skilled artisan.

1
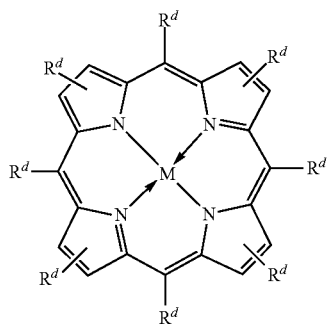

2
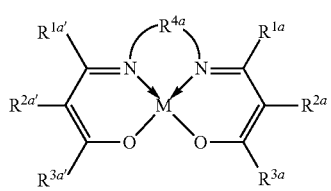

3
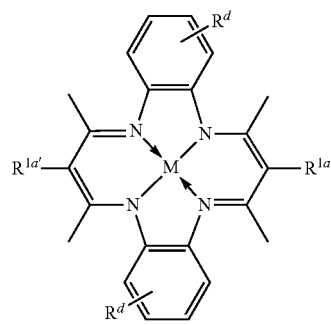

4
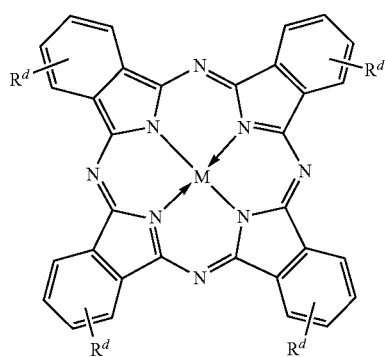

5
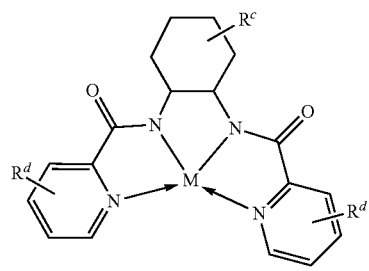

6
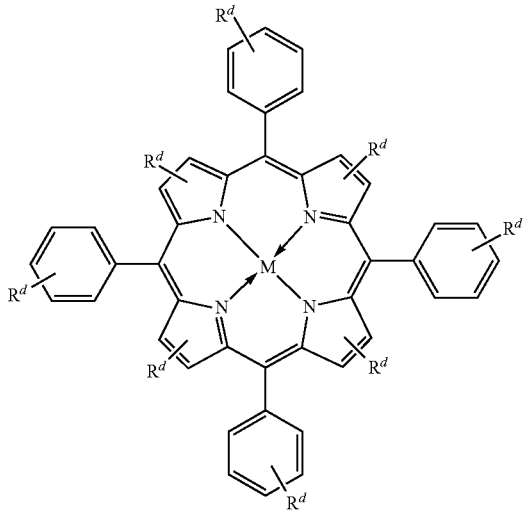

-continued

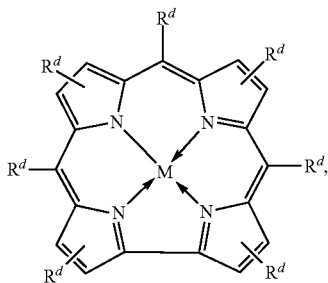

where each of $R^c$, $R^d$, $R^{1a}$, $R^{2a}$, $R^{3a}$, $R^{4a}$, $R^{1a'}$, $R^{2a'}$, $R^{3a'}$, and M, is as defined and described in the classes and subclasses herein.

In some embodiments, Lewis acids provided carbonylation catalysts used in methods described herein comprise metal-porphinato complexes. In some embodiments, the moiety ⊕ has the structure:

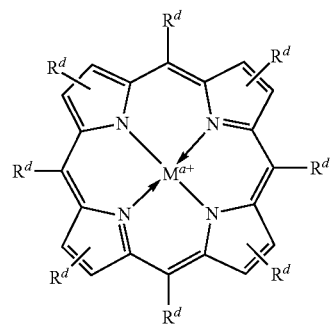

wherein each of M and a is as defined above and described in the classes and subclasses herein, and $R^d$ at each occurrence is independently hydrogen, halogen, —$OR^4$, —$NR^y{}_2$, —$SR^y$, —CN, —$NO_2$, —$SO_2R^y$, —$SOR^y$, —$SO_2NR^y{}_2$; —CNO, —$NR^ySO_2R^y$, —NCO, —$N_3$, —$SiR^y{}_3$; Or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently is a hydroxyl protecting group or $R^y$.

In some embodiments, the moiety ⊕ has the structure:

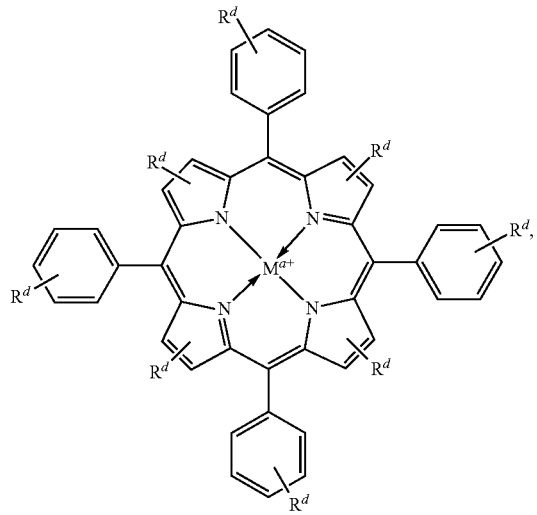

wherein M, a and $R^d$ are as defined above and in the classes and subclasses herein.

In some embodiments, the moiety ⊕ has the structure:

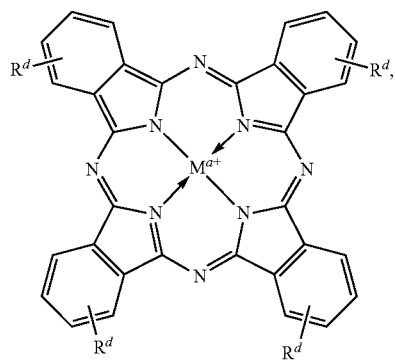

where M, a and $R^d$ are as defined above and in the classes and subclasses herein.

In some embodiments, Lewis acids included in carbonylation catalysts used in methods described herein comprise metallo salenate complexes. In some embodiments, the moiety ⊕ has the structure:

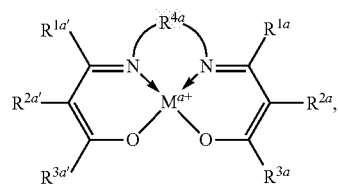

wherein:
M, and a are as defined above and in the classes and subclasses herein.

$R^{1a}$, $R^{1a'}$, $R^{2a}$, $R^{2a'}$, $R^{3a}$, and $R^{3a'}$ are independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more $R^y$ groups; and $R^{4a}$ is selected from the group consisting of:

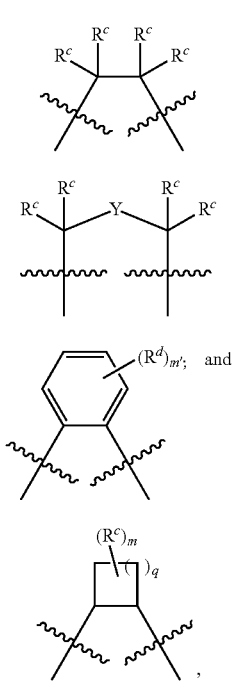

e)

f)

g)

h)

where
$R^c$ at each occurrence is independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

wherein:
two or more $R^c$ groups may be taken together with the carbon atoms to which they are attached and any intervening atoms to form one or more rings;
when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;
wherein $R^4$ and $R^y$ are as defined above and in classes and subclasses herein;
Y is a divalent linker selected from the group consisting of: —$NR^y$—, —$N(R^y)C(O)$—, —$C(O)NR^y$—, —O—, —C(O)—, —OC(O)—, —C(O)O—, —S—, —SO—, —$SO_2$—, —C(=S)—, —C(=$NR^y$)—, —N=N—; a polyether; a $C_3$ to $C_8$ substituted or unsubstituted carbocycle; and a $C_1$ to $C_8$ substituted or unsubstituted heterocycle;
m' is 0 or an integer from 1 to 4, inclusive;
q is 0 or an integer from 1 to 4, inclusive; and
x is 0, 1, or 2.

In some embodiments, a provided Lewis acid comprises a metallo salen compound, as shown in formula Ia:

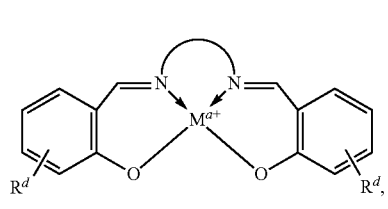

Ia wherein each of M, $R^d$, and a, is as defined above and in the classes and subclasses herein, ⌒ represents is an optionally substituted moiety linking the two nitrogen atoms of the diamine portion of the salen ligand, where ⌒ is selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —$NR^y$—, —$N(R^y)C(O)$—, —$C(O)NR^y$—, —$OC(O)N(R^y)$—, —$N(R^y)C(O)O$—, —$OC(O)O$—, —O—, —C(O)—, —OC(O)—, —C(O)O—, —S—, —SO—, —$SO_2$—, —C(=S)—, —C(=$NR^y$)—, —C(=$NOR^y$)— or —N=N—.

In some embodiments metal complexes having formula Ia above, at least one of the phenyl rings comprising the salicylaldehyde-derived portion of the metal complex is independently selected from the group consisting of:

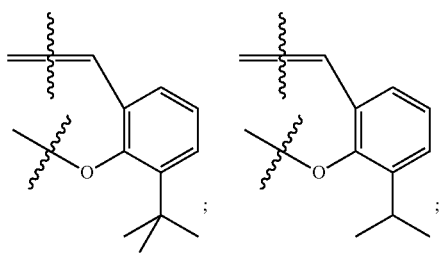

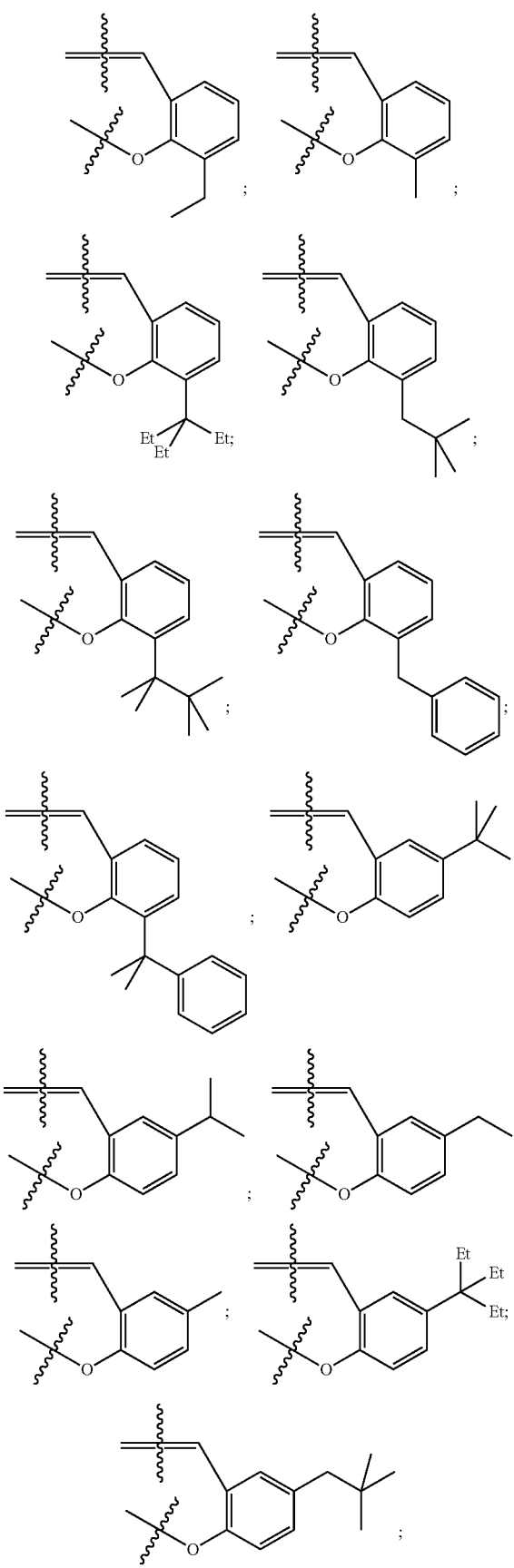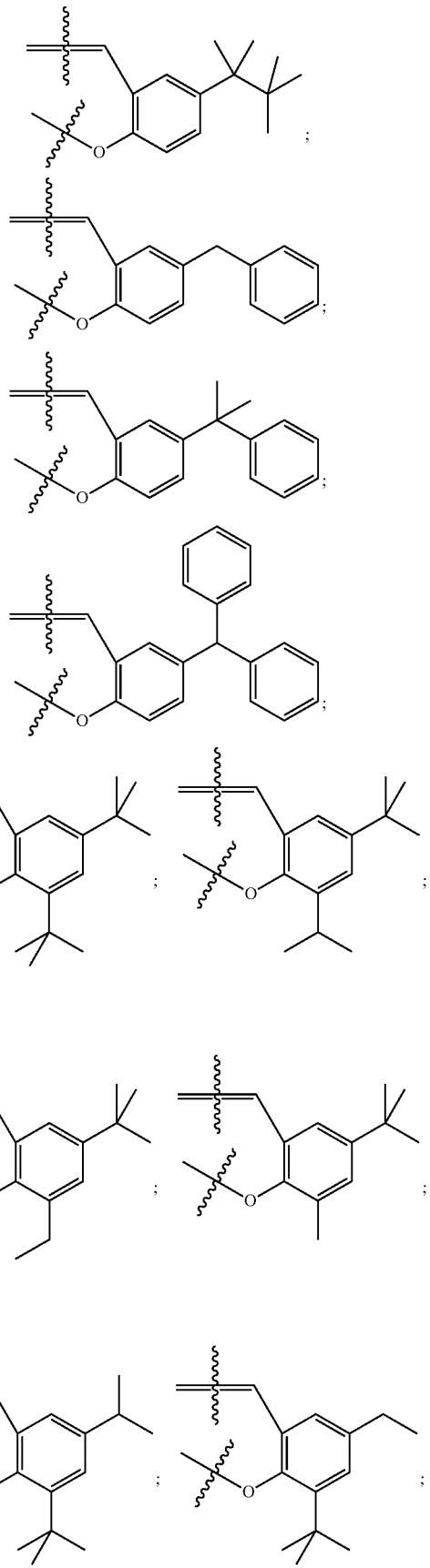

-continued

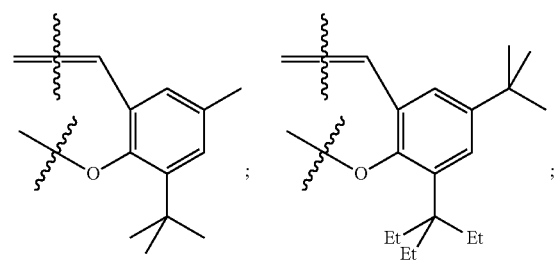

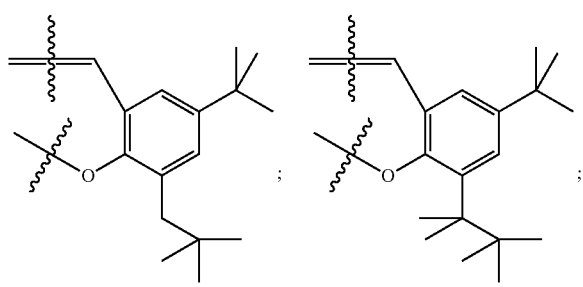

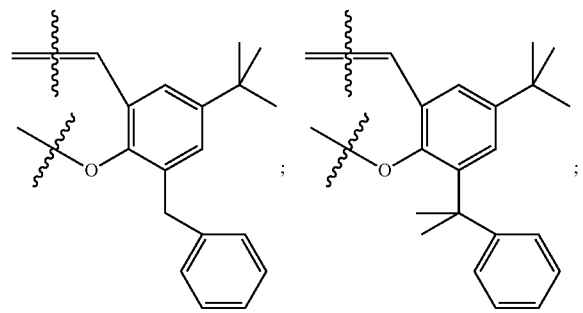

and

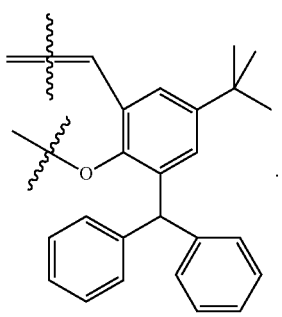

In some embodiments, a provided Lewis acid comprises a metallo salen compound, conforming to one of formulae Va or Vb:

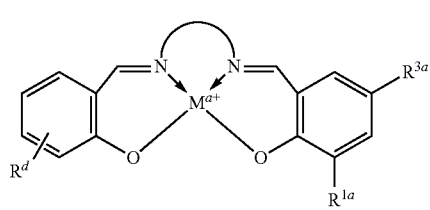

or

-continued

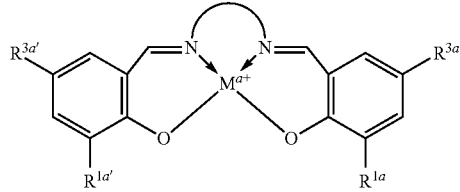

where M, a, $R^d$, $R^{1a}$, $R^{3a}$, $R^{1a'}$, $R^{3a'}$, and ⌢, are as defined above and in the classes and subclasses herein.

In some embodiments of metal complexes having formulae Va or Vb, each $R^{1a}$ and $R^{3a}$ is, independently, optionally substituted $C_1$-$C_{20}$ aliphatic.

In some embodiments, the moiety ⌢ comprises an optionally substituted 1,2-phenyl moiety.

In some embodiments, Lewis acids included in carbonylation catalysts used in methods described herein comprise metal-tmtaa complexes. In some embodiments, the moiety ⊕ has the structure:

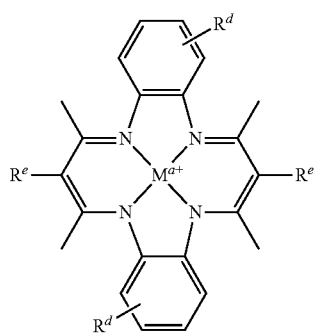

where M, a and $R^d$ are as defined above and in the classes and subclasses herein, and $R^e$ at each occurrence is independently hydrogen, halogen, —OR, —$NR^y_2$, —SR, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety ⊕ has the structure:

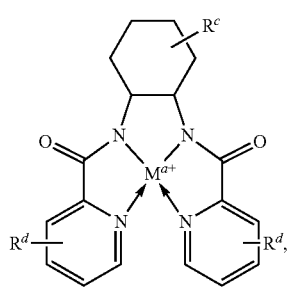

where each of M, a, $R^c$ and $R^d$ is as defined above and in the classes and subclasses herein.

In some embodiments, where carbonylation catalysts used in methods described herein include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments M is Cr(III).

In some embodiments, M has an oxidation state of +4. In some embodiments, M is Ti(IV) or Cr(IV).

In some embodiments, $M^1$ and $M^2$ are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, $M^1$ and $M^2$ are the same. In some embodiments, $M^1$ and $M^2$ are the same metal, but have different oxidation states. In some embodiments, $M^1$ and $M^2$ are different metals.

In some embodiments, one or more of $M^1$ and $M^2$ has an oxidation state of +2. In some embodiments, $M^1$ is Zn(II), Cu(II), Mn(II), Co(II), Ru(II), Fe(II), Co(II), Rh(II), Ni(II), Pd(II) or Mg(II). In some embodiments $M^1$ is Zn(II). In some embodiments $M^1$ is Cu(II). In some embodiments, $M^2$ is Zn(II), Cu(II), Mn(II), Co(II), Ru(II), Fe(II), Co(II), Rh(II), Ni(II), Pd(II) or Mg(II). In some embodiments $M^2$ is Zn(II). In some embodiments $M^2$ is Cu(II).

In some embodiments, one or more of $M^1$ and $M^2$ has an oxidation state of +3. In some embodiments, $M^1$ is Al(III), Cr(III), Fe(III), Co(III), Ti(III) In(III), Ga(III) or Mn(III). In some embodiments $M^1$ is Al(III). In some embodiments $M^1$ is Cr(III). In some embodiments, $M^2$ is Al(III), Cr(III), Fe(III), Co(III), Ti(III) In(III), Ga(III) or Mn(III). In some embodiments $M^2$ is Al(III). In some embodiments $M^2$ is Cr(III).

In some embodiments, one or more of $M^1$ and $M^2$ has an oxidation state of +4. In some embodiments, $M^1$ is Ti(IV) or Cr(IV). In some embodiments, $M^2$ is Ti(IV) or Cr(IV).

In some embodiments, the metal-centered Lewis-acidic component of the carbonylation catalyst includes a dianionic tetradentate ligand. In some embodiments, the dianionic tetradentate ligand is selected from the group consisting of: porphyrin ligand; salen ligand; dibenzotetramethyltetraaza[14]annulene (tmtaa) ligand; phthalocyaninate ligand; and the Trost ligand.

In some embodiments, the carbonylation catalyst includes a carbonyl cobaltate in combination with an aluminum porphyrin compound. In some embodiments, the carbonylation catalyst is [(TPP)Al(THF)$_2$][Co(CO)$_4$] where TPP stands for tetraphenylporphyrin and THF stands for tetrahydrofuran.

In some embodiments, the carbonylation catalyst includes a carbonyl cobaltate in combination with a chromium porphyrin compound.

In some embodiments, the carbonylation catalyst includes a carbonyl cobaltate in combination with a chromium salen compound. In some embodiments, the carbonylation catalyst includes a carbonyl cobaltate in combination with a chromium salophen compound.

In some embodiments, the carbonylation catalyst includes a carbonyl cobaltate in combination with an aluminum salen compound. In some embodiments, the carbonylation catalyst includes a carbonyl cobaltate in combination with an aluminum salophen compound.

In some embodiments, one or more neutral two electron donors coordinate to M $M^1$ or $M^2$ and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

BPL to PPL

In certain embodiments where the BPL conversion comprises polymerizing the BPL, the method includes contacting the BPL with a polymerization catalyst, optionally in the presence of one or more solvents. Suitable solvents can include, for example, hydrocarbons, ethers, esters, ketones, nitriles, amides, sulfones, and halogenated hydrocarbons. In certain embodiments, the solvent is selected such that the polymer formed is soluble in the reaction medium. In certain embodiments, the solvent is selected such that the polymer formed is insoluble, or at least partially insoluble, in the reaction medium.

In certain embodiments where the BPL conversion comprises polymerizing the BPL to form a PPL, the conversion comprises a continuous polymerization. Such continuous polymerizations can be conducted in a continuous stirred tank reactor or a plug flow reactor such that polymer or polymer solution is withdrawn at essentially the same rate it is formed. Polymerization of BPL can be performed with a number of polymerization initiators including for example alcohols, amines, polyols, polyamines, and diols, amongst others. Further, a variety of catalysts may be used in the polymerization reaction, including for example metals (e.g., lithium, sodium, potassium, magnesium, calcium, zinc, aluminum, titanium, cobalt, etc.) metal oxides, carbonates of alkali- and alkaline earth metals, borates, silicates, of various metals. In some variations, catalysts that may be used in the polymerization reaction, include for example metals (e.g., lithium, sodium, potassium, magnesium, calcium, zinc, aluminum, titanium, cobalt, etc.) metal oxides, salts of alkali and alkaline earth metals (such as carbonates, borates, hydroxides, alkoxides, and carboxylates), and borates, silicates, or salts of other metals.

Polymerization Catalysts

Many catalysts are known for the ring-opening polymerization of lactones (such as caprolactone and beta lactones). Any such catalyst can be employed in the BPL polymerization processes described herein.

Catalysts suitable for the ring-opening polymerization of the methods herein are disclosed, for example, in: Journal of the American Chemical Society (2002), 124(51), 15239-15248 *Macromolecules*, vol. 24, No. 20, pp. 5732-5733, *Journal of Polymer Science*, Part A-1, vol. 9, No. 10, pp.

2775-2787; Inoue, S., Y. Tomoi, T. Tsuruta & J. Furukawa; *Macromolecules*, vol. 26, No. 20, pp. 5533-5534; *Macromolecules*, vol. 23, No. 13, pp. 3206-3212; *Polymer Preprints* (1999), 40(1), 508-509; *Macromolecules*, vol. 21, No. 9, pp. 2657-2668; and *Journal of Organometallic Chemistry*, vol. 341, No. 1-3, pp. 83-9; and in U.S. Pat. Nos. 3,678,069, 3,169,945, 6,133,402; 5,648,452; 6,316,590; 6,538,101; and 6,608,170.

In certain embodiments, suitable catalysts include carboxylate salts of metal ions or organic cations. In certain embodiments, a carboxylate salt is other than a carbonate.

In certain embodiments, the polymerization catalyst is combined with BPL in a molar ratio up to about 1:100,000 polymerization catalyst:BPL. In certain embodiments, the ratio is from about 1:100,000 to about 25:100 polymerization catalyst:BPL. In certain embodiments, the polymerization catalyst is combined with BPL in a molar ratio of about 1:50,000 polymerization catalyst:BPL to about 1:25,000 polymerization catalyst:BPL. In certain embodiments, the polymerization catalyst is combined with BPL in a molar ratio of about 1:25,000 polymerization catalyst:BPL to about 1:10,000 polymerization catalyst:BPL. In certain embodiments, the polymerization catalyst is combined with BPL in a molar ratio of about 1:20,000 polymerization catalyst:BPL to about 1:10,000 polymerization catalyst:BPL. In certain embodiments, the polymerization catalyst is combined with BPL in a molar ratio of about 1:15,000 polymerization catalyst:BPL to about 1:5,000 polymerization catalyst:BPL. In certain embodiments, the polymerization catalyst is combined with BPL in a molar ratio of about 1:5,000 polymerization catalyst:BPL to about 1:1,000 polymerization catalyst:BPL. In certain embodiments, the polymerization catalyst is combined with BPL in a molar ratio of about 1:2,000 polymerization catalyst:BPL to about 1:500 polymerization catalyst:BPL. In certain embodiments, the polymerization catalyst is combined with BPL in a molar ratio of about 1:1,000 polymerization catalyst:BPL to about 1:200 polymerization catalyst:BPL. In certain embodiments, the polymerization catalyst is combined with BPL in a molar ratio of about 1:500 polymerization catalyst:BPL to about 1:100 polymerization catalyst:BPL. In certain embodiments the molar ratio of polymerization catalyst:BPL is about 1:50,000, 1:25,000, 1:15,000, 1:10,000, 1:5,000, 1:1,000, 1:500, 1:250 or a range including any two of these values. In certain embodiments the molar ratio of polymerization catalyst:BPL is about 1:100, 5:100, 10:100, 15:100, 20:100, 25:100 or a range including any two of these values. In certain embodiments, the polymerization catalyst is combined with BPL in a molar ratio of about 1:100 polymerization catalyst:BPL to about 25:100 polymerization catalyst:BPL. In certain embodiments the molar ratio of polymerization catalyst:BPL is about 1:100, 5:100, 10:100, 15:100, 20:100, 25:100 or a range including any two of these values. In certain embodiments where the polymerization catalyst comprises a carboxylate salt, the carboxylate has a structure such that upon initiating polymerization of BPL, the polymer chains produced have an acrylate chain end. In certain embodiments, the carboxylate ion on a polymerization catalyst is the anionic form of a chain transfer agent (CTA) used in the polymerization process.

In certain embodiments, the carboxylate salt of the polymerization catalyst is an acrylate salt (i.e., the anionic form) of a compound

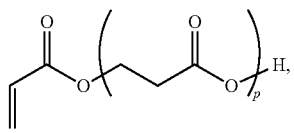

or a mixture of any two or more of these, where p is from 0 to 9. In certain embodiments, p is from 0 to 5. In certain embodiments, the carboxylate salt of the polymerization catalyst is an acrylate salt (i.e., of compound above where p=0).

In certain embodiments, the carboxylate salt of the polymerization catalyst is a salt of an acrylic acid dimer:

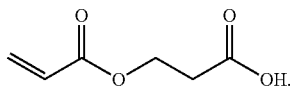

In certain embodiments, the carboxylate salt of the polymerization catalyst is a salt of an acrylic acid trimer,

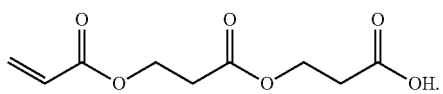

In certain embodiments, where the polymerization catalyst comprises a carboxylate salt, the carboxylate is the anionic form of a $C_{1-40}$ carboxylic acid. In certain embodiments, the carboxylate salt can be a salt of a polycarboxylic acid (e.g. a compound having two or more carboxylic acid groups). In certain embodiments, the carboxylate comprises the anion of a $C_{1-20}$ carboxylic acid. In certain embodiments, the carboxylate comprises the anion of a $C_{1-12}$ carboxylic acid. In certain embodiments, the carboxylate comprises the anion of a $C_{1-8}$ carboxylic acid. In certain embodiments, the carboxylate comprises the anion of a $C_{1-4}$ carboxylic acid. In certain embodiments, the carboxylate comprises the anion of an optionally substituted benzoic acid. In certain embodiments, the carboxylate is selected from the group consisting of: formate, acetate, propionate, valerate, butyrate, $C_{5-10}$ aliphatic carboxylate, and $C_{10-20}$ aliphatic carboxylate.

As noted, in certain embodiments, the polymerization catalyst comprises a carboxylate salt of an organic cation. In certain embodiments, the polymerization catalyst comprises a carboxylate salt of a cation wherein the positive charge is located at least partially on a nitrogen, sulfur, or phosphorus atom. In certain embodiments, the polymerization catalyst comprises a carboxylate salt of a nitrogen cation. In certain embodiments, the polymerization catalyst comprises a carboxylate salt of a cation selected from the group consisting of: ammonium, amidinium, guanidinium, a cationic form of a nitrogen heterocycle, and any combination of two or more of these. In certain embodiments, the polymerization catalyst comprises a carboxylate salt of a phosphorus cation. In certain embodiments, the polymerization catalyst comprises a carboxylate salt of a cation selected from the group consisting of: phosphonium and phosphazenium. In certain embodiments, the polymerization catalyst comprises a carboxylate salt of a sulfur-containing cation. In certain embodiments, the polymerization catalyst comprises a sulfonium salt.

In certain embodiments, the polymerization catalyst comprises a carboxylate salt of a metal. In certain embodiments, the polymerization catalyst comprises a carboxylate salt of a alkali or alkaline earth metal. In certain embodiments, the polymerization catalyst comprises a carboxylate salt of an alkali metal. In certain embodiments, the polymerization catalyst comprises a carboxylate salt of sodium or potassium. In certain embodiments, the polymerization catalyst comprises a carboxylate salt of sodium.

In certain embodiments, the polymerization catalyst comprises a carboxylate salt of a protonated amine:

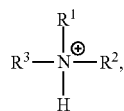

where:
each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms; and each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings.

In certain embodiments where the polymerization catalyst comprises a carboxylate salt of a protonated amine, the protonated amine is selected from the group consisting of:

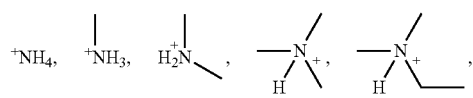

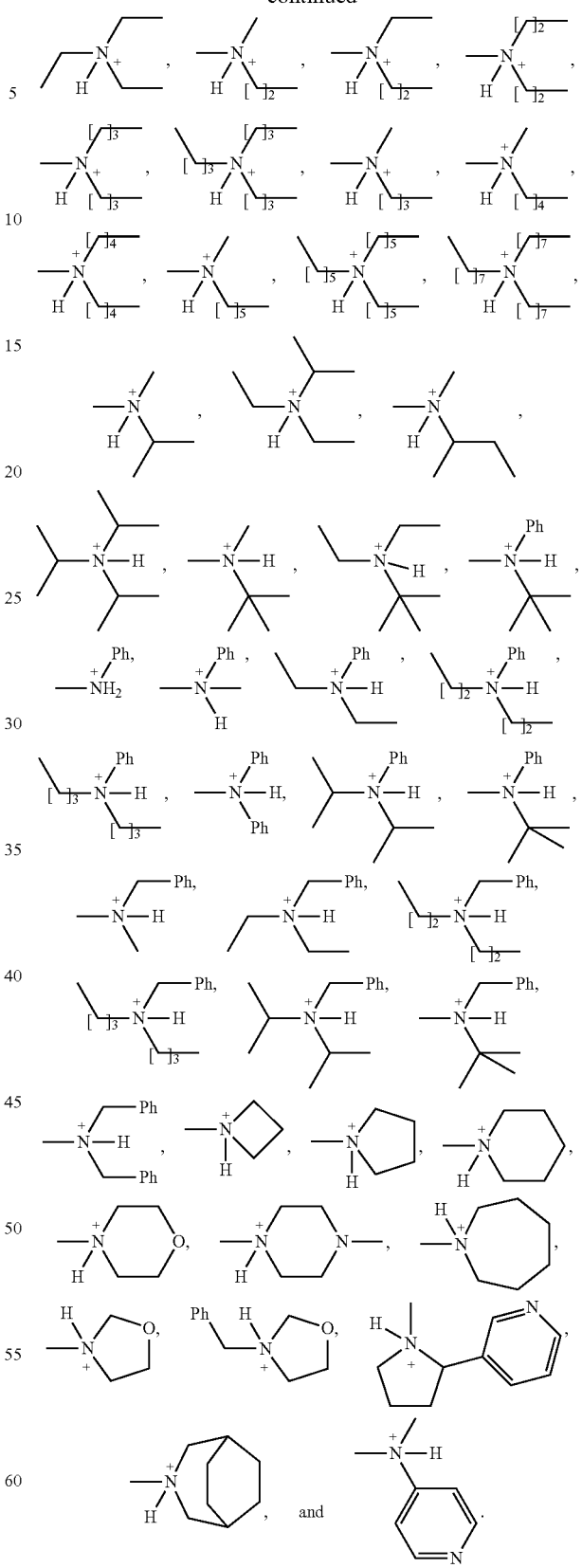

In certain embodiments, the polymerization catalyst comprises a carboxylate salt of a quaternary ammonium salt:

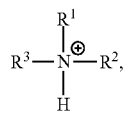

where:
  each $R^1$, $R^2$ and $R^3$ is described above; and
  each $R^4$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^4$ group can be taken with an $R^1$, $R^2$ or $R^3$ group to form one or more optionally substituted rings.

In certain embodiments, a polymerization catalyst comprises a carboxylate salt of a guanidinium group:

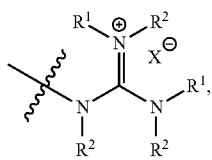

wherein each $R^1$ and $R^2$ is independently as defined above and described in classes and subclasses herein. In certain embodiments, each $R^1$ and $R^2$ is independently hydrogen or $C_{1-20}$ aliphatic. In certain embodiments, each $R^1$ and $R^2$ is independently hydrogen or $C_{1-12}$ aliphatic. In certain embodiments, each $R^1$ and $R^2$ is independently hydrogen or $C_{1-20}$ heteroaliphatic. In certain embodiments, each $R^1$ and $R^2$ is independently hydrogen or phenyl. In certain embodiments, each $R^1$ and $R^2$ is independently hydrogen or 8- to 10-membered aryl. In certain embodiments, each $R^1$ and $R^2$ is independently hydrogen or 5- to 10-membered heteroaryl. In certain embodiments, each $R^1$ and $R^2$ is independently hydrogen or 3- to 7-membered heterocyclic. In certain embodiments, one or more of $R^1$ and $R^2$ is optionally substituted $C_{1-2}$ aliphatic.

In certain embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In certain embodiments, three or more $R^1$ and/or $R^2$ groups are taken together to form an optionally substituted fused ring system.

In certain embodiments, an $R^1$ and $R^2$ group are taken together with intervening atoms to form a compound selected from:

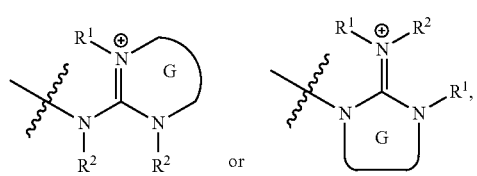

wherein each $R^1$ and $R^2$ is independently as defined above and described in classes and subclasses herein, and Ring G is an optionally substituted 5- to 7-membered saturated or partially unsaturated heterocyclic ring.

It will be appreciated that when a guanidinium cation is depicted as

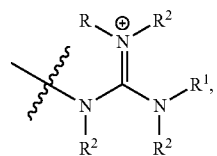

all such resonance forms are contemplated and encompassed by the present disclosure. For example, such groups can also be depicted as

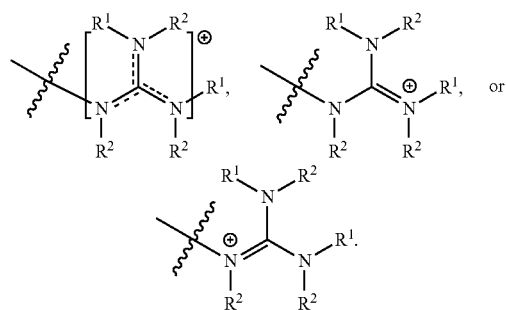

In specific embodiments, a guanidinium cation is selected from the group consisting of:

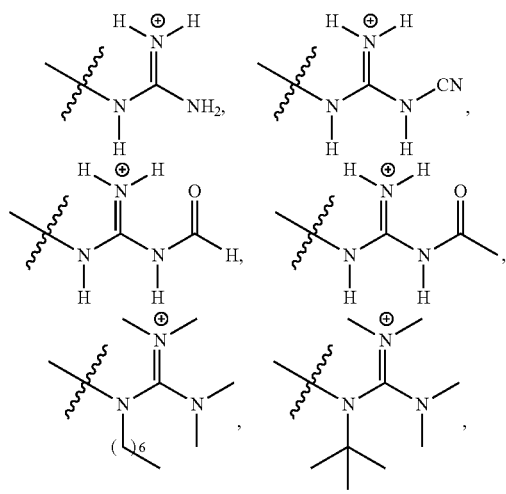

-continued

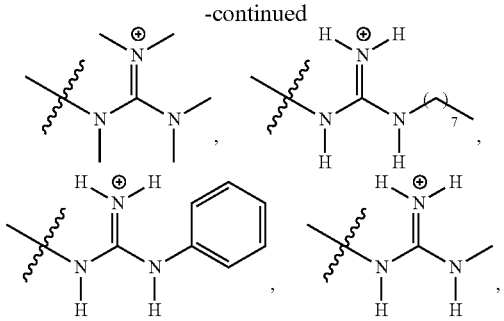

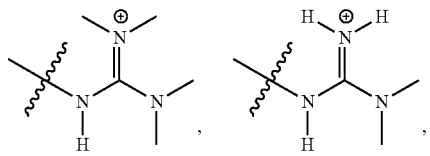

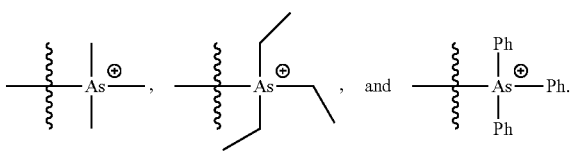

In certain embodiments, a polymerization catalyst comprises a carboxylate salt of a sulfonium group or an arsonium group, such as

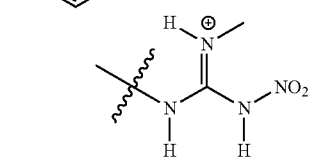

wherein each of $R^1$, $R^2$, and $R^3$ are as defined above and described in classes and subclasses herein.

In specific embodiments, an arsonium cation is selected from the group consisting of:

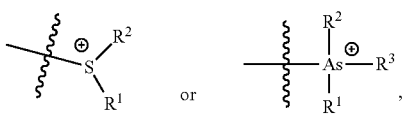

In certain embodiments, a polymerization catalyst comprises a carboxylate salt of an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In certain embodiments, a nitrogen-containing heterocycle includes a quaternarized nitrogen atom. In certain embodiments, a nitrogen-containing heterocycle includes an iminium moiety such as

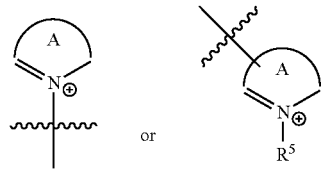

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In certain embodiments, a ring nitrogen to which the attachment is made is thereby quaternized, and In certain embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In certain embodiments, a polymerization catalyst comprises a carboxylate salt of

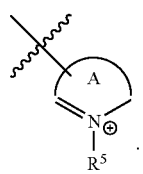

In certain embodiments, ring A is an optionally substituted, 5- to 10-membered heteroaryl group. In certain embodiments, Ring A is an optionally substituted, 6-membered heteroaryl group. In certain embodiments, Ring A is a ring of a fused heterocycle. In certain embodiments, Ring A is an optionally substituted pyridyl group.

In specific embodiments, a nitrogen-containing heterocyclic cation is selected from the group consisting of:

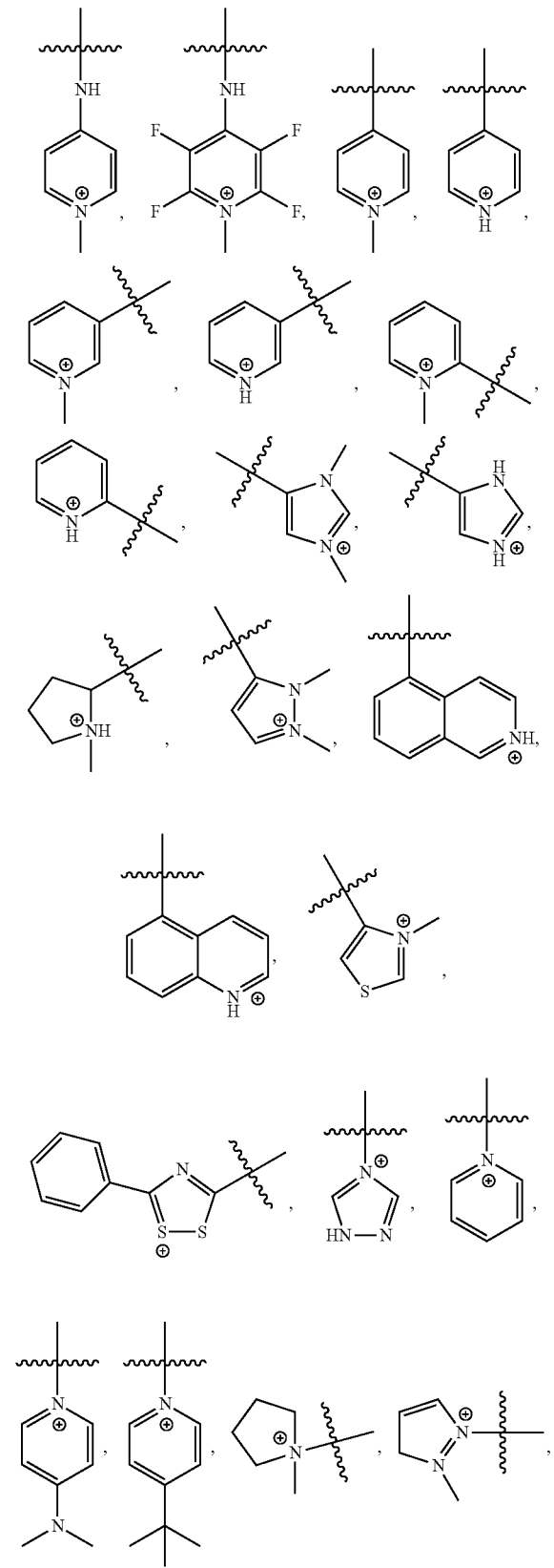

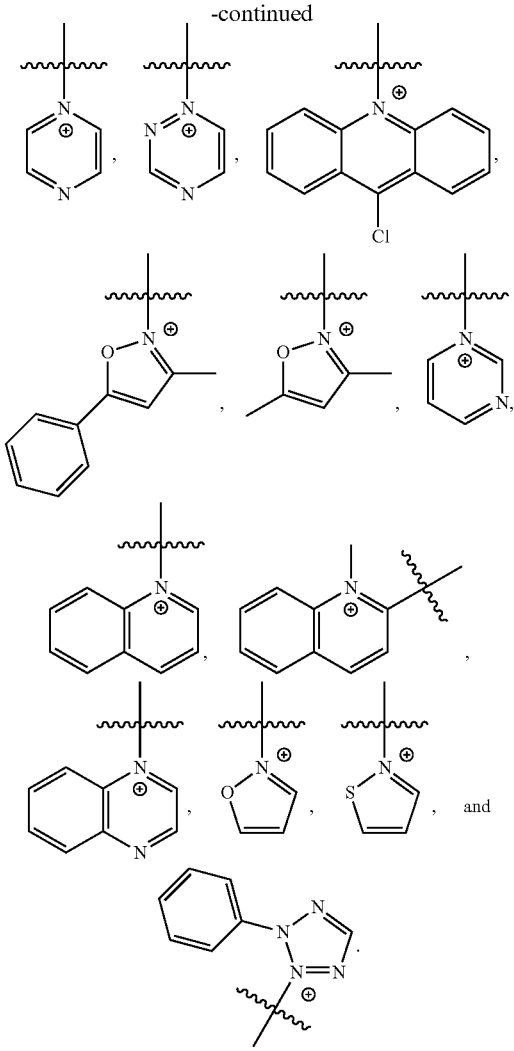

and

In certain embodiments, a polymerization catalyst comprises a carboxylate salt of

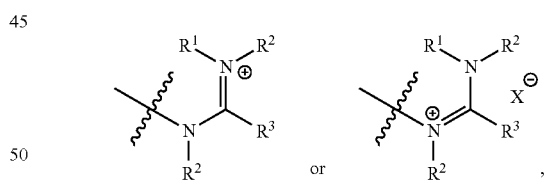

where each $R^1$, $R^2$, and $R^3$ is independently as defined above and described in classes and subclasses herein.

In certain embodiments, a polymerization catalyst comprises a carboxylate salt of

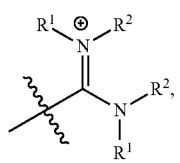

wherein each $R^1$ and $R^2$ is independently as defined above and described in classes and subclasses herein.

In certain embodiments, a polymerization catalyst comprises a carboxylate salt of

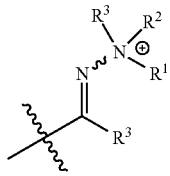

wherein each $R^1$, $R^2$, and $R^3$ is independently as defined above and described in classes and subclasses herein.

In certain embodiments, a polymerization catalyst comprises a carboxylate salt of

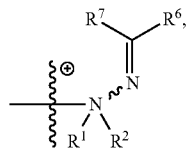

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In certain embodiments, $R^6$ and $R^7$ are each independently an optionally substituted $C_{1-20}$ aliphatic. In certain embodiments, $R^6$ and $R^7$ are each independently an optionally substituted $C_{1-20}$ heteroaliphatic having. In certain embodiments, $R^6$ and $R^7$ are each independently an optionally substituted phenyl or 8-10-membered aryl. In certain embodiments, $R^6$ and $R^7$ are each independently an optionally substituted 5- to 10-membered heteroaryl. In certain embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In certain embodiments, $R^6$ and $R^7$ are each independently an optionally substituted $C_{1-6}$ aliphatic. In certain embodiments, each occurrence of $R^6$ and $R^7$ is independently methyl, ethyl, propyl, butyl, pentyl, hexyl, heptyl, octyl, or benzyl. In certain embodiments, each occurrence of $R^6$ and $R^7$ is independently perfluoro. In certain embodiments, each occurrence of $R^6$ and $R^7$ is independently —$CF_2CF_3$.

In certain embodiments, a polymerization catalyst comprises a carboxylate salt of

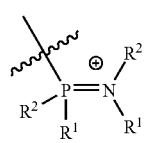

wherein each $R^1$ and $R^2$ is independently as defined above and described in classes and subclasses herein.

In certain embodiments, a polymerization catalyst comprises a carboxylate salt of

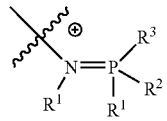

wherein each $R^1$, $R^2$, and $R^3$ is independently as defined above and described in classes and subclasses herein.

In certain embodiments, a cation is

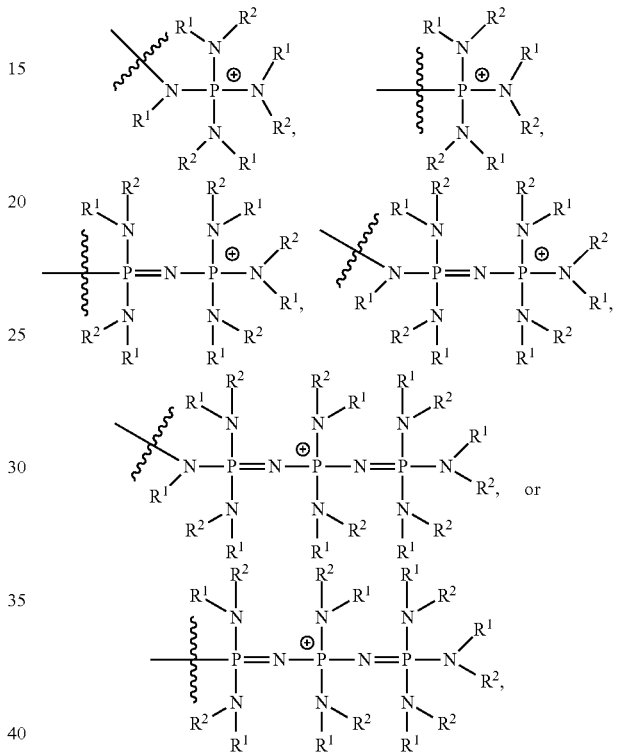

wherein each $R^1$ and $R^2$ is independently as defined above and described in classes and subclasses herein.

In certain embodiments, a polymerization catalyst comprises a carboxylate salt of

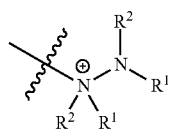

wherein each $R^1$ and $R^2$ is independently as defined above and described in classes and subclasses herein.

In certain embodiments, a polymerization catalyst comprises a carboxylate salt of

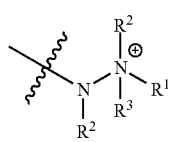

wherein each $R^1$, $R^2$, and $R^3$ is independently as defined above and described in classes and subclasses herein.

In certain embodiments, a polymerization catalyst comprises a carboxylate salt of

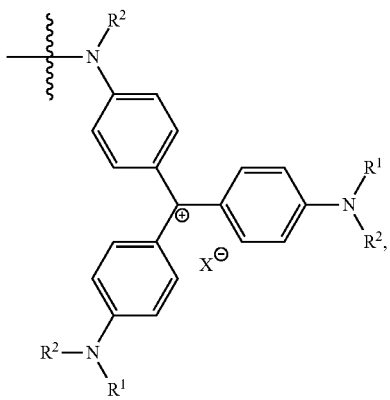

wherein each $R^1$ and $R^2$ is independently as defined above and described in classes and subclasses herein. In certain embodiments, suitable catalysts include transition metal compounds. In certain embodiments, suitable catalysts include acid catalysts. In certain embodiments, the catalyst is a heterogeneous catalyst.

In certain embodiments, the carboxylate salt of the polymerization catalyst is a compound:

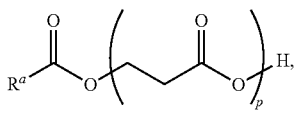

where p is from 0 to 9 and $R^a$ is a non-volatile moiety. The term "non-volatile moiety," as used herein, refers to a moiety or material to which a carboxylate can be attached, and that renders the carboxylate (e.g., when p=0) non-volatile to pyrolysis conditions. In certain embodiments, a non-volatile moiety is selected from the group consisting of glass surfaces, silica surfaces, plastic surfaces, metal surfaces including zeolites, surfaces containing a metallic or chemical coating, membranes (e.g., nylon, polysulfone, silica), microbeads (e.g., latex, polystyrene, or other polymer), and porous polymer matrices (e.g., polyacrylamide, polysaccharide, polymethacrylate). In certain embodiments, a non-volatile moiety has a molecular weight above 100, 200, 500, or 1000 g/mol. In certain embodiments, a non-volatile moiety is part of a fixed or packed bed system. In certain embodiments, a non-volatile moiety is part of a fixed or packed bed system comprising pellets (e.g., zeolite).

In certain embodiments, p is from 0 to 5. In certain embodiments, the carboxylate salt of the polymerization catalyst is an acrylate salt (i.e., of the above compound where p=0).

In certain embodiments, a suitable carboxylate catalyst is heterogeneous. In certain embodiments, a suitable carboxylate catalyst will remain in a reaction zone as a salt or melt after removal of all other products, intermediates, starting materials, byproducts, and other reaction components. In certain embodiments, a suitable carboxylate catalyst (i.e., the above compound where p is from 0 to 9) will remain in a reaction zone as a salt or melt after removal of all AA product stream.

In certain embodiments, a catalyst is recycled for further use in a reaction zone. In certain embodiments, a salt or melt catalyst is recycled to a reaction zone. In certain embodiments, provided methods further comprise withdrawing a recycling stream of homogeneous catalyst to a reaction zone. In certain embodiments, such a recycling stream comprises a high boiling solvent, wherein the solvent's boiling point is above the pyrolysis temperature of PPL and the catalyst remains in the high boiling solvent during pyrolysis while the withdrawn product stream is gaseous.

In some variations of the foregoing, the catalyst recycling stream has less than 0.01 wt % of oxygen. In certain variations, the catalyst recycling stream has less than 0.005 wt % oxygen. In certain variations, the catalyst recycling stream has less than 200 ppm oxygen. In certain variations, the catalyst recycling stream has less than 150 ppm oxygen, less than 100 ppm oxygen, less than 50 ppm oxygen, less than 20 ppm oxygen, less than 10 ppm oxygen, less than 5 ppm oxygen, less than 2 ppm oxygen, or less than 1 ppm oxygen. In certain variations, the catalyst recycling stream has less than 0.05 wt % water. In certain variations, the catalyst recycling stream has less than 0.01 wt % water. In certain variations, the catalyst recycling stream has less than 1000 ppm water. In certain variations, the catalyst recycling stream has less than 500 ppm water, less than 400 ppm water, less than 250 ppm water, less than 200 ppm water, less than 150 ppm water, less than 100 ppm water, less than 50 ppm water, or less than 10 ppm water. In certain variations, the catalyst recycling stream has less than 200 ppm of oxygen and water combined.

PPL to AA

In some embodiments, BPL is converted to AA (e.g., GAA) without isolation of the intermediate PPL, wherein the PPL formed by polymerization of BPL is concurrently converted to AA (e.g., GAA) via pyrolysis in the same reaction zone (e.g., a "one-pot" method). In certain embodiments, the reaction zone containing the reaction of BPL to PPL is maintained at a temperature at or above the pyrolysis temperature of PPL such that the thermal decomposition of PPL produces AA. Without wishing to be bound by any particular theory, it is believed that in such embodiments as BPL reacts with AA to start polymer chains, thermal decomposition will degrade the polymer to AA.

A one-pot BPL conversion to AA can be operated within a variety of temperature and pressure ranges. In certain embodiments, the temperature can range from about 150° C. to about 300° C. In certain embodiments, the temperature ranges from about 150° C. to about 200° C. In certain embodiments, the temperature ranges from about 150° C. to about 250° C. In certain embodiments, the temperature ranges from about 175° C. to about 300° C. n some embodiments, the temperature ranges from about 200° C. to about 250° C. In certain embodiments, the temperature ranges from about 225° C. to about 275° C. In certain embodiments, the temperature ranges from about 250° C. to about 300° C. In certain embodiments, the temperature ranges from about 200° C. to about 300° C.

In certain embodiments, the pressure used in provided methods and systems can range from about 0.01 atmospheres to about 500 atmospheres (absolute). In certain embodiments, the pressure can range from about 0.01 atmospheres to about 10 atmospheres (absolute). In certain embodiments, the pressure can range from about 0.01 atmospheres to about 50 atmospheres (absolute). In certain embodiments, the pressure can range from about 1 atmosphere to about 10 atmospheres (absolute). In certain embodiments, the pressure can range from about 1 atmosphere to about 50 atmospheres (absolute). In certain embodiments, the pressure can range from about 1 atmosphere to about 100 atmospheres (absolute). In certain embodiments, the pressure can range from about 10 atmospheres to about 50 atmospheres (absolute). In certain embodiments, the pressure can range from about 10 atmospheres to about 100 atmospheres (absolute). In certain embodiments, the pressure can range from about 50 atmospheres to about 100 atmospheres (absolute). In certain embodiments, the pressure can range from about 50 atmospheres to about 200 atmospheres (absolute). In certain embodiments, the pressure can range from about 100 atmospheres to about 200 atmospheres (absolute). In certain embodiments, the pressure can range from about 100 atmospheres to about 250 atmospheres (absolute). In certain embodiments, the pressure can range from about 200 atmospheres to about 300 atmospheres (absolute). In certain embodiments, the pressure can range from about 200 atmospheres to about 500 atmospheres (absolute). In certain embodiments, the pressure can range from about 250 atmospheres to about 500 atmospheres (absolute).

In some embodiments, the pressure used in provided methods and systems for converting PPL to AA is less than about 5 atmospheres (absolute). In some embodiments, the pressure used in provided methods and systems is less than about 1 atmosphere (absolute). In some embodiments, the pressure can range from about 0.01 atmospheres to about 1 atmosphere (absolute). In some embodiments, the pressure can range from about 0.1 atmospheres to about 0.8 atmospheres (absolute). In some embodiments, the pressure can range from about 0.1 atmospheres to about 0.5 atmospheres (absolute). In some embodiments, the pressure can range from about 0.01 atmospheres to about 0.1 atmospheres (absolute). In some embodiments, the pressure can range from about 0.4 atmospheres to about 1 atmosphere (absolute). In some embodiments, the pressure can range from about 0.05 atmospheres to about 0.1 atmospheres (absolute).

The conversion of PPL to AA can be operated within a variety of temperature and pressure ranges. In certain embodiments, the temperature can range from about 150° C. to about 300° C. In certain embodiments, the temperature ranges from about 150° C. to about 200° C. In certain embodiments, the temperature ranges from about 150° C. to about 250° C. In certain embodiments, the temperature ranges from about 175° C. to about 300° C. n some embodiments, the temperature ranges from about 200° C. to about 250° C. In certain embodiments, the temperature ranges from about 225° C. to about 275° C. In certain embodiments, the temperature ranges from about 250° C. to about 300° C. In certain embodiments, the temperature ranges from about 200° C. to about 300° C.

The conversion of PPL to AA can be performed in a variety of apparatus. In certain embodiments, the conversion of PPL to AA is performed in a continuous reactor. In certain embodiments, the continuous reactor is selected from a continuous stirred tank reactor, a plug flow reactor, and a combination of two or more of these. In certain embodiments, the continuous reactor is selected from the group consisting of a wiped film evaporator, a falling film evaporator, a loop reactor, a fluidized bed reactor, a circulating fluidized bed reactor a devolatilizing extruder, a vented tubular reactor and a heavy oil reactor. In certain embodiments, the conversion of PPL to AA comprises a wiped film evaporator. In certain embodiments, the conversion of PPL to AA comprises a falling film evaporator. In certain embodiments, the conversion of PPL to AA comprises a fluidized bed reactor. In certain embodiments, the conversion of PPL to AA comprises a devolatilizling extruder. In certain embodiments, the conversion of PPL to AA comprises a circulating fluidized bed reactor.

AA to PAA & SAPs

Monomeric AA (including GAA) precursors of SAPs must react to completion or nearly so to prevent or minimize the presence of residual unreacted monomer in the SAP or products, such as diapers, made from the SAP. In some embodiments, AA and PAA, or a salt thereof, made from the disclosed systems and methods are substantially free from compounds that derives from the oxidation of propylene and/or aldehyde impurities. As such, the disclosed AA reacts more fully to produce PAA, sodium polyacrylate and other co-polymers, having minimal or substantially no residual unreacted AA, suitable for incorporated into SAPs.

As used herein, the term "superabsorbent polymer" (SAP) refers to a water-swellable, water-insoluble polymer capable, under the most favorable conditions, of absorbing at least about 10 times its weight in an aqueous solution containing 0.9 weight percent sodium chloride. A SAP's ability to absorb water may depend on the ionic concentration of the aqueous solution. In deionized and distilled water, a SAP may absorb 500 times its weight (from 30 to 60 times its own volume) and can become up to 99.9% liquid, but when put into a 0.9% saline solution, the absorbency may drop to 50 times its weight.

SAPs are generally made from the polymerization of AA blended with sodium hydroxide in the presence of a radical initiator (e.g., azobisisobutyronitrile, AIBN) to form a PAA sodium salt (sometimes referred to as sodium polyacrylate). This polymer is presently among the most common types of SAPs. Other materials are also used to make a SAP, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile, among others. SAPs are generally made using one of three methods: gel polymerization, suspension polymerization or solution polymerization.

Gel Polymerization: A mixture of frozen acrylic acid, water, cross-linking agents and UV initiator chemicals are blended and placed either on a moving belt or in large tubs. The liquid mixture then goes into a "reactor" which may be a long chamber with a series of strong UV lights. The UV radiation drives the polymerization and cross-linking reactions. The resulting "logs" may be sticky gels containing 60-70% water. The logs are shredded or ground and placed in various sorts of driers. Additional cross-linking agent may be sprayed on the particles' surface; this "surface cross-linking" increases the product's ability to swell under pressure—a property measured as Absorbency Under Load (AUL) or Absorbency Against Pressure (AAP). The dried polymer particles are then screened for proper particle size distribution and packaging. The gel polymerization (GP) method is widely used for making the sodium polyacrylate superabsorbent polymers now used in baby diapers and other disposable hygienic articles.

Solution Polymerization: Solution polymers offer the absorbency of a granular polymer supplied in solution form. Solutions can be diluted with water prior to application, and can coat most substrates or used to saturate them. After drying at a specific temperature for a specific time, the result is a coated substrate with superabsorbency. For example, this chemistry can be applied directly onto wires and cables, though it is especially optimized for use on components such as rolled goods or sheeted substrates.

Solution-based polymerization is commonly used today for SAP manufacture of co-polymers, particularly those with the toxic acrylamide monomer. This process is efficient and generally has a lower capital cost base. The solution process uses a water-based monomer solution to produce a mass of reactant polymerized gel. The polymerization's own exothermic reaction energy is used to drive much of the process, helping reduce manufacturing cost. The reactant polymer gel is then chopped, dried and ground to its final granule size. Treatments to enhance performance characteristics of the SAP are often accomplished after the final granule size is created.

Suspension Polymerization: generally requires a higher degree of production control and product engineering during the polymerization step. This process suspends the water-based reactant in a hydrocarbon-based solvent. The net result is that the suspension polymerization creates the primary polymer particle in the reactor rather than mechanically in post-reaction stages. Performance enhancements can also be made during, or just after, the reaction stage.

In selected embodiments, SAPs prepared from PAA, sodium polyacrylate, and AA that derive from the systems and methods described herein, have less than about 1000, 500, 200, 100, 50 or 10 parts per million residual monoethylenically unsaturated monomer, which for example may derive from an unsaturated AA monomer.

Large Scale AA Production

In another aspect, a system is provided for the production of AA, e.g., an AA production plant, wherein the system produces AA at a rate of about 200 to about 1,000 kilotons per annum (kta). Presently in the art, because of limits on the equipment required to control heat and remove impurities in the propylene oxidation process, modern acrylic acid plants generate approximately 160 kta AA from propylene-based feedstock. Without being bound by theory, the disclosed systems are capable of producing greater output of AA from ethylene-based feedstock. In certain embodiments, the system produces the acrylic acid (AA) from ethylene. In certain embodiments, the AA is crude AA. In certain embodiments, the AA is glacial AA. In some embodiments, the AA is substantially free of a product or by product of propylene oxidation. In some embodiments, the AA is substantially free of an aldehyde impurity. In some embodiments, the AA is substantially free of furfural. In some embodiments, the AA is substantially free of acetic acid. In some embodiments, the AA is substantially free of stabilizers. In some embodiments, the AA is substantially free of radical polymerization inhibitors. In some embodiments, the AA is substantially free of anti-foam agents.

Specifically, the disclosed systems include a reactor for the oxidation of ethylene to EO, a reactor for carbonylating EO with CO to produce BPL, and reactors for converting BPL to AA, optionally via PPL.

In certain embodiments, the system produces AA at a rate of about 200, 250, 300, 350, 400, 450, 500, 550, 600, 650, 700, 750, 800, 850, 900, 950, 1,000 kta, or within a range including any two of these values.

In another aspect, a method is provided for the production of acrylic acid (AA) from ethylene in a single integrated system, the method comprising:
providing ethylene to an oxidative reactor that converts at least some of the ethylene to ethylene oxide (EO),
providing EO to a central reactor that converts at least some of the EO to beta propiolactone (BPL),
and at least one of the following steps:
providing BPL to a first reactor that converts at least some of the BPL to AA, and
providing BPL to a reactor that converts at least some of the BPL to polypropiolactone (PPL), and
isolating acrylic acid at a rate of about 200 to about 800 kilotons per annum (kta).

In some variations, provided is a method for producing acrylic acid (AA) from ethylene in a single integrated system, the method comprising:
providing ethylene to an oxidative reactor that converts at least some of the ethylene to ethylene oxide (EO),
providing EO to a central reactor that converts at least some of the EO to beta propiolactone (BPL),
at least the following (i) or (ii), or both (i) and (ii):
(i) providing BPL to a first reactor that converts at least some of the BPL to AA, or
(ii) providing BPL to a reactor that converts at least some of the BPL to polypropiolactone (PPL) which is optionally fed to a reactor that converts PPL to AA; and
(d) producing acrylic acid at a rate of about 200 to about 800 kilotons per annum (kta).

The term "integrated system" as used herein means a single system such as a chemical plant, confined to a single geographic location, and comprising an abutting series of reactors or system components.

Enumerated Embodiments

The following enumerated embodiments are representative of some aspects of the invention.

1. A system for the production of polyacrylic acid (PAA) from ethylene, comprising: an oxidative reactor, comprising an inlet fed by ethylene, an oxidative reaction zone that converts at least some of the ethylene to ethylene oxide (EO), and an outlet which provides an outlet stream comprising the EO,
a central reactor, comprising an inlet fed by an EO source, and a carbon monoxide (CO) source, a central reaction zone that converts at least some of the EO to beta propiolactone (BPL) or polypropiolactone (PPL), and an outlet which provides an outlet stream comprising the BPL or PPL,
one or more of (i), (ii) and (iii):
  (i) a first reactor, comprising an inlet fed by the outlet stream comprising BPL of the central reactor, a first reaction zone that converts at least some of the BPL to AA, and an outlet which provides an outlet stream comprising the AA,
  (ii) a second (a) reactor, comprising an inlet fed by the outlet stream comprising BPL of the central reactor, a second (a) reaction zone that converts at least some of the BPL to PPL, and an outlet which provides an outlet stream comprising the PPL, and a second (b) reactor, comprising an inlet fed by the outlet stream comprising PPL of the second (a) reactor, a second (b) reaction zone that converts at least some of the PPL to AA, and an outlet which provides an outlet stream comprising the AA, and
  (iii) a third reactor, comprising an inlet fed by the outlet stream comprising PPL of the central reactor, a third reaction zone that converts at least some of the PPL to a third product, and an outlet which provides an outlet stream comprising the AA, and
  (iv) a fourth reactor, comprising an inlet fed by the outlet stream comprising AA of one or more of the first, second (b) and third reactor, a fourth reaction zone that converts at least some of the AA to polyacrylic acid (PAA), or a salt thereof, and an outlet which provides an outlet stream comprising the PAA, or a salt thereof, and a controller for independently modulating production of the EO, BPL, PPL, AA and PAA.

2. The system of embodiment 1, comprising two of (i), (ii) and (iii).
3. The system of embodiment 1, comprising three of (i), (ii) and (iii).
4. The system of embodiment 1, wherein the system produces AA at about 200 to about 800 kilotons per annum (kta).
5. The system of embodiment 1, wherein the AA is glacial acrylic acid (GAA).
6. The system of embodiment 5, wherein the GAA is substantially free of an aldehyde impurity or a compound that derives from the oxidation of propylene.
7. The system of embodiment 1, wherein the inlet to the fourth reactor is fed by one or more reactant streams comprising sodium hydroxide in the presence of a radical initiator to form a PAA sodium salt.
8. The system of embodiment 1, wherein at least some of the AA is converted to the PAA, or a salt thereof, via gel polymerization, suspension polymerization or solution polymerization.
9. The system of embodiment 1, wherein the PAA, or a salt thereof, is substantially free of an aldehyde impurity or a compound that derives from the oxidation of propylene.
10. The system of embodiment 1, wherein the inlet to the fourth reactor is further fed by one or more reactant streams each comprising a monomer to co-polymerize with GAA to form one or more co-polymers of PAA selected from a polyacrylamide copolymer, ethylene maleic anhydride copolymer, cross-linked carboxymethylcellulose copolymer, polyvinyl alcohol copolymer, cross-linked polyethylene oxide copolymer, and starch grafted polyacrylonitrile copolymer of PAA.
11. The system of embodiment 1, further comprising:
    (v) a fifth reactor, comprising an inlet fed by the outlet stream comprising PAA, or a salt thereof, of the fourth reactor, a fifth reaction zone that converts at least some of the PAA, or a salt thereof, to superabsorbent polymer (SAP) and an outlet which provides an outlet stream comprising the SAP.
12. The system of embodiment 11, wherein the inlet to the fifth reactor is further fed by one or more reactant streams each comprising a cross-linking agent may be sprayed on the PAA, or a salt thereof.
13. The system of embodiment 11, wherein the SAP comprises less than about 1000 parts per million residual monoethylenically unsaturated monomer, and is substantially free of an aldehyde impurity or a compound that derives from the oxidation of propylene.
14. An article comprising the SAP of embodiment 11.
15. The article of embodiment 14, wherein the article is a disposable diaper.
16. A method, wherein the method is for the conversion of ethylene to acrylic acid (AA) within an integrated system, the method comprising the steps of:
    providing an inlet stream comprising ethylene to an oxidative reactor of the integrated system to effect conversion of at least a portion of the provided ethylene to EO,
    providing an inlet stream comprising EO, from the oxidative reactor, and carbon monoxide (CO) to a central reactor of the integrated system,
    contacting the inlet stream with a metal carbonyl in a central reaction zone to effect conversion of at least a portion of the provided EO to a beta propiolactone (BPL), directing an outlet stream comprising BPL from the central reaction zone to at least one of:
        (i) a first reactor, comprising an inlet fed by the outlet stream comprising BPL of the central reactor, a first reaction zone that converts at least some of the BPL to AA, and an outlet from which an outlet stream comprising the AA is obtainable,
        (ii) a second (a) reactor, comprising an inlet fed by the outlet stream comprising BPL of the central reactor, a second (a) reaction zone that converts at least some of the BPL to PPL, and an outlet from which an outlet stream comprising the PPL is obtainable, and a second (b) reactor, comprising an inlet fed by the outlet stream comprising PPL of the second (a) reactor, a second (b) reaction zone that converts at least some of the PPL to AA, and an outlet from which an outlet stream comprising the AA is obtainable,
        (iii) a third reactor, comprising an inlet fed by the outlet stream comprising PPL of the central reactor, a third reaction zone that converts at least some of the PPL to a third product, and an outlet from which an outlet stream comprising the AA is obtainable, and
    obtaining AA; and
    providing an outlet stream comprising GAA from one or more of the first, second (b) and third reactor, to the inlet of (iv) a fourth reactor in which at least some of the GAA is converted to polyacrylic acid (PAA), or a salt thereof.
17. The method of embodiment 16, wherein the AA is glacial acrylic acid (GAA).
18. The method of embodiment 17, wherein the GAA is substantially free of an aldehyde impurity or a compound that derives from the oxidation of propylene.
19. The method of embodiment 16, wherein the PAA is substantially free of an aldehyde impurity or a compound that derives from the oxidation of propylene.
20. The method of embodiment 16, further comprising:
    providing an outlet stream comprising PAA, or a salt thereof, from the fourth reactor, to the inlet of (v) a fifth reactor in which at least some of the PAA, or a salt thereof, is converted to superabsorbent polymer (SAP).
21. The method of embodiment 20, wherein the SAP comprises less than about 1000 parts per million residual monoethylenically unsaturated monomer.
22. The method of embodiment 16, wherein the GAA is converted to PAA less than one week after the ethylene is converted to EO.
23. The method of embodiment 16, wherein the GAA is converted to PAA less than two days after the ethylene is converted to EO.
24. A system for producing polyacrylic acid (PAA) from ethylene, comprising:
    an oxidative reactor, comprising:
        an inlet configured to receive ethylene,
        an oxidative reaction zone configured to convert at least some of the ethylene to ethylene oxide (EO), and
        an outlet configured to provide an EO stream comprising the EO;
    a central reactor, comprising:
        an inlet configured to receive EO from the EO stream of the oxidative reactor, and carbon monoxide (CO) from a CO source, a central reaction zone configured to convert at least some of the EO to beta propiolactone (BPL) or polypropiolactone (PPL), or a combination thereof, and an outlet configured to provide a carbonylation stream comprising the BPL, or a carbonylation stream comprising the PPL, or a combination thereof;

one or more of (i), (ii) and (iii):
   (i) a first reactor, comprising:
      an inlet configured to receive BPL from the carbonylation stream of the central reactor,
      a first reaction zone configured to convert at least some of the BPL to AA, and
      an outlet configured to provide an AA stream comprising the AA,
   (ii) a second (a) reactor, comprising:
      an inlet configured to receive BPL from the carbonylation stream of the central reactor,
      a second (a) reaction zone configured to convert at least some of the BPL to PPL, and
      an outlet configured to provide a PPL stream comprising the PPL, and
   a second (b) reactor, comprising:
      an inlet configured to receive the PPL stream of the second (a) reactor,
      a second (b) reaction zone configured to convert at least some of the PPL to AA, and
      an outlet configured to provide an AA stream comprising the AA, and
   (iii) a third reactor, comprising:
      an inlet configured to receive PPL from carbonylation stream of the central reactor,
      a third reaction zone configured to convert at least some of the PPL to AA, and
      an outlet configured to provide an AA stream comprising the AA;
a fourth reactor, comprising:
   an inlet configured to receive the AA stream of one or more of the first, second (b) and third reactor,
   a fourth reaction zone configured to convert at least some of the AA to polyacrylic acid (PAA), or a salt thereof, and
   an outlet configured to provide a PAA stream comprising the PAA, or a salt thereof; and
a controller to independently modulate production of the EO, BPL, PPL, AA and PAA.

25. The system of embodiment 24, comprising two of (i), (ii) and (iii).

26. The system of embodiment 24, comprising three of (i), (ii) and (iii).

27. The system of any one of embodiments 24 to 26, wherein the system produces AA at about 200 to about 800 kilotons per annum (kta).

28. The system of any one of embodiments 24 to 27, wherein the AA is glacial acrylic acid (GAA).

29. The system of any one of embodiments 24 to 27, wherein the AA is substantially free of an aldehyde impurity or a compound that derives from the oxidation of propylene.

30. The system of any one of embodiments 24 to 27, wherein the AA has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight of an aldehyde impurity or a compound that derives from the oxidation of propylene.

31. The system of any one of embodiments 24 to 27, wherein the AA has less than 10,000 ppm, 1,000 ppm, 500 ppm, 100 ppm, 50 ppm, 10 ppm of an aldehyde impurity or a compound that derives from the oxidation of propylene.

32. The system of any one of embodiments 24 to 31, wherein the inlet to the fourth reactor is configured to receive one or more reactant streams comprising sodium hydroxide, and the fourth reaction zone is configured to form a PAA sodium salt from the one or more reactant streams in the presence of a radical initiator.

33. The system of any one of embodiments 24 to 32, wherein the fourth reaction zone is configured to convert at least some of the AA to polyacrylic acid (PAA), or a salt thereof, by gel polymerization, suspension polymerization, or solution polymerization.

34. The system of any one of embodiments 24 to 33, wherein the PAA, or a salt thereof, is substantially free of an aldehyde impurity or a compound that derives from the oxidation of propylene.

35. The system of any one of embodiments 24 to 33, wherein the PAA has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight of an aldehyde impurity or a compound that derives from the oxidation of propylene.

36. The system of any one of embodiments 24 to 33, wherein the PAA has less than 10,000 ppm, 1,000 ppm, 500 ppm, 100 ppm, 50 ppm, 10 ppm of an aldehyde impurity or a compound that derives from the oxidation of propylene.

37. The system of any one of embodiments 24 to 36, wherein the inlet to the fourth reactor is configured to further receive one or more reactant streams each comprising a coreactant to co-polymerize with AA, and the fourth reaction zone is configured to form one or more co-polymers of PAA selected from a polyacrylamide copolymer, ethylene maleic anhydride copolymer, cross-linked carboxymethylcellulose copolymer, polyvinyl alcohol copolymer, cross-linked polyethylene oxide copolymer, and starch grafted polyacrylonitrile copolymer of PAA.

38. The system of any one of embodiments 24 to 37, further comprising:
   a fifth reactor, comprising:
      an inlet configured to receive PAA, or a salt thereof, from the PAA stream of the fourth reactor,
      a fifth reaction zone configured to convert at least some of the PAA, or a salt thereof, to superabsorbent polymer (SAP), and
      an outlet configured to provide a SAP stream comprising the SAP.

39. The system of embodiment 38, wherein the inlet to the fifth reactor is configured to further receive one or more reactant streams each comprising a cross-linking agent.

40. The system of embodiment 38 or 39, wherein the SAP has less than about 1000 parts per million residual monoethylenically unsaturated monomer.

41. The system of any one of embodiments 38 to 40, wherein the SAP is substantially free of an aldehyde impurity or a compound that derives from the oxidation of propylene.

42. The system of any one of embodiments 38 to 40, wherein the SAP has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight of an aldehyde impurity or a compound that derives from the oxidation of propylene.

43. The system of any one of embodiments 38 to 40, wherein the SAP has less than 10,000 ppm, 1,000 ppm, 500 ppm, 100 ppm, 50 ppm, 10 ppm of an aldehyde impurity or a compound that derives from the oxidation of propylene.

44. A method for converting ethylene to polyacrylic acid (PAA) within an integrated system, the method comprising:
providing an ethylene stream comprising ethylene to an oxidative reactor of the integrated system;
converting at least a portion of the ethylene in the ethylene stream to ethylene oxide (EO) in the oxidative reactor to produce an EO stream comprising the EO;
providing the EO stream from the oxidative reactor, and a carbon monoxide (CO) stream comprising CO to a central reaction zone of the integrated system;
contacting the EO stream and the CO stream with a metal carbonyl in the central reaction zone;
converting at least a portion of the EO in the EO stream to beta propiolactone (BPL) or polypropiolactone (PPL), or a combination thereof, in the central reaction zone to produce a carbonylation stream comprising BPL, or a carbonylation stream comprising PPL, or a combination thereof;
(i) directing the carbonylation stream comprising BPL to an AA reactor, and converting at least some of the BPL in the carbonylation stream to AA in the AA reactor to produce an AA stream comprising the AA; or
(ii) directing the carbonylation stream comprising BPL to a PPL reactor, converting at least some of the BPL in the carbonylation stream to PPL in the PPL reactor to produce a PPL stream comprising PPL, directing the PPL stream to an AA reactor (also referred to in FIG. 1 as second (b) reactor), and converting at least some of the PPL to AA in the AA reactor to produce an AA stream; or
(iii) directing the carbonylation stream comprising PPL to an AA reactor, and converting at least some of the PPL in the carbonylation stream to AA in the AA reactor to produce an AA stream comprising AA; or
any combinations of (i)-(iii) above;
directing the AA streams of (i)-(iii) above to a PAA reactor; and
converting at least a portion of the AA of the AA streams of (i)-(iii) above to polyacrylic acid (PAA), or a salt thereof, in the PAA reactor.

45. The method of embodiment 44, comprising two of (i), (ii) and (iii).

46. The method of embodiment 44, comprising three of (i), (ii) and (iii).

47. The method of any one of embodiments 44 to 46, wherein AA is produced at about 200 to about 800 kilotons per annum (kta).

48. The method of any one of embodiments 44 to 47, wherein the AA is glacial acrylic acid (GAA).

49. The method of any one of embodiments 44 to 47, wherein the AA is substantially free of an aldehyde impurity or a compound that derives from the oxidation of propylene.

50. The method of any one of embodiments 44 to 47, wherein the AA has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight of an aldehyde impurity or a compound that derives from the oxidation of propylene.

51. The method of any one of embodiments 44 to 47, wherein the AA has less than 10,000 ppm, 1,000 ppm, 500 ppm, 100 ppm, 50 ppm, 10 ppm of an aldehyde impurity or a compound that derives from the oxidation of propylene.

52. The method of any one of embodiments 44 to 51, wherein the PAA is substantially free of an aldehyde impurity or a compound that derives from the oxidation of propylene.

53. The method of any one of embodiments 44 to 51, wherein the PAA has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight of an aldehyde impurity or a compound that derives from the oxidation of propylene.

54. The method of any one of embodiments 44 to 51, wherein the PAA has less than 10,000 ppm, 1,000 ppm, 500 ppm, 100 ppm, 50 ppm, 10 ppm of an aldehyde impurity or a compound that derives from the oxidation of propylene.

55. The method of any one of embodiments 44 to 54, further comprising:
providing a PAA stream comprising the PAA, or a salt thereof, from the PAA reactor;
directing the PAA stream to a superabsorbent polymer (SAP) reactor; and
converting at least a portion of the PAA in the PAA stream to SAP in the SAP reactor.

56. The method of embodiment 55, wherein the SAP has less than about 1000 parts per million residual monoethylenically unsaturated monomer.

57. The method of any one of embodiments 44 to 56, wherein the AA is converted to PAA less than one week after the ethylene is converted to EO.

58. The method of any one of embodiments 44 to 56, wherein the AA is converted to PAA less than two days after the ethylene is converted to EO.

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An integrated system for producing polyacrylic acid (PAA) and superabsorbent polymer (SAP) from ethylene, comprising:
an oxidative reactor, comprising:
an inlet configured to receive ethylene,
an oxidative reaction zone configured to convert ethylene to ethylene oxide (EO), and
an outlet configured to provide an EO stream comprising the EO;
a central reactor, comprising:
an inlet configured to receive EO from the EO stream of the oxidative reactor, and carbon monoxide (CO) from a CO source,
a central reaction zone configured to convert EO to beta propiolactone (BPL) or polypropiolactone (PPL), or a combination thereof, and an outlet configured to provide a carbonylation stream comprising the BPL, or a carbonylation stream comprising the PPL, or a combination thereof;

one or more of (i), (ii) and (iii):
(i) a first reactor, comprising:
an inlet configured to receive BPL from the carbonylation stream of the central reactor,
a first reaction zone configured to convert BPL to acrylic acid (AA), and
an outlet configured to provide an AA stream comprising the AA,
(ii) a second (a) reactor, comprising:
an inlet configured to receive BPL from the carbonylation stream of the central reactor,
a second (a) reaction zone configured to convert BPL to PPL, and
an outlet configured to provide a PPL stream comprising the PPL, and
a second (b) reactor, comprising:
an inlet configured to receive the PPL stream of the second (a) reactor,
a second (b) reaction zone configured to convert at least some of the PPL to AA, and
an outlet configured to provide an AA stream comprising the AA, and
(iii) a third reactor, comprising:
an inlet configured to receive PPL from the carbonylation stream of the central reactor,
a third reaction zone configured to convert PPL to AA, and
an outlet configured to provide an AA stream comprising the AA;
a fourth reactor, comprising:
an inlet configured to receive the AA stream of one or more of the first, second (b) and third reactor,
a fourth reaction zone configured to convert AA to polyacrylic acid (PAA), or a salt thereof, and
an outlet configured to provide a PAA stream comprising the PAA, or a salt thereof;
a fifth reactor, comprising:
an inlet configured to receive PAA, or a salt thereof, from the PAA stream of the fourth reactor,
a fifth reaction zone configured to directly convert the PAA, or a salt thereof, to superabsorbent polymer (SAP), and
an outlet configured to provide a SAP stream comprising the SAP; and
a controller to independently modulate production of the EO, BPL, PPL, AA, PAA and SAP.

2. The system of claim 1, comprising two of (i), (ii) and (iii).

3. The system of claim 1, comprising (i), (ii) and (iii).

4. The system of claim 1, wherein the system produces AA at 200 kilotons to 800 kilotons per annum (kta).

5. The system of claim 1, wherein the AA has less than 5% by weight of an aldehyde impurity or a compound that derives from the oxidation of propylene.

6. The system of claim 1, wherein the inlet to the fourth reactor is configured to receive one or more reactant streams comprising sodium hydroxide, and the fourth reaction zone is configured to form a PAA sodium salt from the one or more reactant streams in the presence of a radical initiator.

7. The system of claim 1, wherein the fourth reaction zone is configured to convert AA to polyacrylic acid (PAA), or a salt thereof, by gel polymerization, suspension polymerization, or solution polymerization.

8. The system of claim 1, wherein the PAA, or a salt thereof, has less than 5% by weight of an aldehyde impurity or a compound that derives from the oxidation of propylene.

9. The system of claim 1, wherein the inlet to the fourth reactor is configured to further receive one or more reactant streams each comprising a co-reactant to co-polymerize with AA, and the fourth reaction zone is configured to form one or more co-polymers of PAA selected from the group consisting of a polyacrylamide co-polymer, ethylene maleic anhydride co-polymer, cross-linked carboxymethylcellulose co-polymer, polyvinyl alcohol co-polymer, cross-linked polyethylene oxide co-polymer, and starch grafted polyacrylonitrile co-polymer of PAA.

10. The system of claim 1, wherein the inlet to the fifth reactor is configured to further receive one or more reactant streams each comprising a cross-linking agent.

11. The system of claim 1, wherein the SAP has less than 1000 parts per million residual monoethylenically unsaturated monomer, and has less than 5% by weight of an aldehyde impurity or a compound that derives from the oxidation of propylene.

12. The system of claim 1, wherein the controller independently modulates production of the BPL by the central reactor.

13. The system of claim 1, wherein the AA stream has:
less than 1000 parts per million residual monoethylenically unsaturated monomer,
(ii) less than 5% by weight or less than 10,000 ppm of an aldehyde impurity,
(iii) less than 5% by weight or less than 10,000 ppm of a compound that derives from the oxidation of propylene,
(iv) less than 5% by weight or less than 10,000 ppm of furfural,
(v) less than 5% by weight or less than 10,000 ppm of acetic acid,
(vi) less than 5% by weight or less than 10,000 ppm of stabilizers,
(vii) less than 5% by weight or less than 10,000 ppm of radical polymerization inhibitors,
(viii) less than 5% by weight or less than 10,000 ppm of anti-foam agents,
or any combination of (i)-(viii).

* * * * *